United States Patent
Noji et al.

(10) Patent No.: US 10,018,627 B2
(45) Date of Patent: *Jul. 10, 2018

(54) METHOD FOR SEALING SUBSTANCES, METHOD FOR DETECTING TARGET MOLECULE, ARRAY, KIT, AND TARGET MOLECULE DETECTION DEVICE

(71) Applicant: Japan Science and Technology Agency, Kawaguchi-shi, Saitama (JP)

(72) Inventors: Hiroyuki Noji, Saitama (JP); Lisa Yamauchi, Tokyo (JP)

(73) Assignee: JAPAN SCIENCE AND TECHNOLOGY AGENCY, Kawaguchi-Shi (JP)

( * ) Notice: Subject to any disclaimer, the term of this patent is extended or adjusted under 35 U.S.C. 154(b) by 0 days.

This patent is subject to a terminal disclaimer.

(21) Appl. No.: 14/513,660

(22) Filed: Oct. 14, 2014

(65) Prior Publication Data

US 2015/0087547 A1     Mar. 26, 2015

(30) Foreign Application Priority Data

Jul. 8, 2014  (JP) ................. 2014-140700

(51) Int. Cl.
*G01N 33/543*  (2006.01)

(52) U.S. Cl.
CPC . *G01N 33/54313* (2013.01); *G01N 33/54393* (2013.01)

(58) Field of Classification Search
CPC .......... C12Q 1/68; C12P 19/34; C40B 30/04; G01N 33/54

See application file for complete search history.

(56) References Cited

U.S. PATENT DOCUMENTS

| 7,214,540 B2 * | 5/2007 | DeLucas ............. B01J 19/0046 436/174 |
| 9,329,174 B2 | 5/2016 | Noji et al. |
| 2004/0208792 A1 * | 10/2004 | Linton ................. B01L 3/5025 422/552 |

(Continued)

FOREIGN PATENT DOCUMENTS

| CN | 1862260 A | 11/2006 |
| CN | 101947124 A | 1/2011 |

(Continued)

OTHER PUBLICATIONS

Sigma data sheet, Down loaded from the internet [www.sigma-aldrich.com]; printed on Mar. 26, 2017, p. 1.*

(Continued)

*Primary Examiner* — Narayan Bhat

(57) ABSTRACT

A technique for efficiently sealing many substances, such as beads, nucleic acid, protein, virus, cells, and lipid membrane complex, into an array is provided.

The present invention provides a method for sealing a substance, including: (i) a step of introducing a first solvent containing a substance on a substrate on which a plurality of receptacles capable of storing the substance are formed separated from each other by a side wall; and (ii) a step of introducing a second solvent having a greater specific gravity than that of the first solvent onto the first solvent, the step (ii) being carried out after the step (i).

11 Claims, 14 Drawing Sheets
(5 of 14 Drawing Sheet(s) Filed in Color)

(56) References Cited

U.S. PATENT DOCUMENTS

| | | | |
|---|---|---|---|
| 2006/0254933 | A1 | 11/2006 | Adachi et al. |
| 2009/0166206 | A1 | 7/2009 | Hattori |
| 2009/0246782 | A1* | 10/2009 | Kelso ............... B01L 3/502761 435/6.16 |
| 2009/0280251 | A1 | 11/2009 | De Guzman et al. |
| 2010/0022414 | A1 | 1/2010 | Link et al. |
| 2011/0065086 | A1 | 3/2011 | Bruno |
| 2011/0172118 | A1 | 7/2011 | Kain |
| 2011/0212848 | A1* | 9/2011 | Duffy ............... G01N 33/54313 506/9 |
| 2013/0204076 | A1 | 8/2013 | Han et al. |
| 2013/0345088 | A1 | 12/2013 | Noji et al. |

FOREIGN PATENT DOCUMENTS

| | | |
|---|---|---|
| EP | 2 685 266 A1 | 1/2014 |
| EP | 2 891 886 A1 | 7/2015 |
| JP | 2004-309405 A | 11/2004 |
| JP | 2008-111798 A | 5/2008 |
| JP | 2009-109213 A | 5/2009 |
| JP | 2009-162549 A | 7/2009 |
| JP | 2010-054335 A | 3/2010 |
| WO | 2005/021151 A1 | 3/2005 |
| WO | WO2007/120241 * | 10/2007 |
| WO | 2011/079176 A2 | 6/2011 |
| WO | 2011109379 A1 | 9/2011 |
| WO | 2011/160430 A1 | 12/2011 |
| WO | 2012/045012 A2 | 4/2012 |
| WO | 2012121310 A1 | 9/2012 |

OTHER PUBLICATIONS

China Patent and Trademark Office (China) "Office Action" and "Search Report," issued in Chinese Patent Application No. 201280012033.7, which is a Chinese counterpart application to U.S. Appl. No. 14/003,509, with an issuance date of Feb. 13, 2013.

Snapshot of the website "http://www.agc.com/kagaku/shinsei/cytop/en/about.html" maintained by Asahi Glass Co., Ltd., accessed and printed on Jun. 2, 2014.

Extended European Search Report received for European Patent Application No. 12754743.8 dated Nov. 7, 2013, 5 pages.

International Search Report received for PCT Patent Application No. PCT/JP2012/055884, dated May 22, 2012, 5 pages (2 pages of English Translation and 3 pages of PCT search report).

Written Opinion received for PCT Patent Application No. PCT/JP2012/055884, dated May 22, 2012, 4 pages (Japanese Language Only) See Statement Under 37 CFR § 1.98(a) (3).

International Preliminary Report on Patentability received for PCT Patent Application No. PCT/JP2012/055884, completed on Jan. 31, 2013, 11 pages (4 pages of English Translation and 7 pages of IPRP).

Rissin et al., "Single-Molecule Enzyme-Linked Immunosorbent Assay Detects Serum Proteins at Subfemtomolar Concentrations", Nature Biotechnology, vol. 28, No. 6, Jun. 2010, pp. 595-599.

Sakakihara et al., "A Single-Molecule Enzymatic Assay in a Directly Accessible Femtoliter Droplet Array", The Royal Society of Chemistry, Lab Chip, vol. 10, 2010, pp. 3355-3362.

Chambers: Dictionary of Science and Technology, general editor Professor Peter M B Walker, CBE, FRSE, Chambers Harrap Publishers Ltd. p. 1150 (1999).

Snapshot of the website "http://www.sigmaaldrich.com/catalog/product/aldrich/469629?lang=en&region=US" maintained by Sigma-Aldrich Co. LLC, accessed and printed on Aug. 26, 2014.

Snapshot of the website "http://www.sigmaaldrich.com/catalog/product/aldrich/469610?lang=en&region=US" maintained by Sigma-Aldrich Co. LLC, accessed and printed on Aug. 26, 2014.

International Search Report received for PCT Patent Application No. PCT/JP2015/003310 dated Aug. 11, 2015, 2 pages.

United States Patent and Trademark Office, Office Action, issued in U.S. Appl. No. 14/003,509, of which U.S. Appl. No. 14/513,660 is a continuation-in-part application, with a notification date of Jun. 29, 2015, 19 pages.

United States Patent and Trademark Office, Office Action, issued in U.S. Appl. No. 14/003,509, with a notification date of Mar. 7, 2014, 11 pages.

United States Patent and Trademark Office, Office Action, issued in U.S. Appl. No. 14/003,509, with a notification date of Jul. 1, 2014, 9 pages.

S. Capizzi and J. Schwartzbrod, "Surface properties of Ascaris suum eggs: hydrophobic potential and Lewis acid-base interactions", Colloids and Surfaces B: Biointerfaces, vol. 22, pp. 99-105 (2001), Elsevier Science B.V.

Andrew D. Griffiths and Dan S. Tawfik, "Directed evolution of an extremely fast phosphotriesterase by in vitro compartmentalization", The EMBO Journal, vol. 22, No. 1, pp. 24-35 (2003).

Jacqueline R. Retting and Albert Folch, "Large-Scale Single-Cell Trapping and Imaging Using Microwell Arrays", Analytical Chemistry, vol. 77, pp. 5628-5634 (2005), American Chemical Society.

Yannick Rondelez et al., "Microfabricated arrays of femtoliter chambers allow single molecule enzymology", Nature Biotechnology, vol. 23, No. 3, pp. 361-365 (Mar. 2005).

United States Patent and Trademark Office, Office Action, issued in U.S. Appl. No. 14/003,509, of which U.S. Appl. No. 14/513,660 is a continuation-in-part application, with a notification date of Dec. 11, 2014, 19 pages.

Alan U. Larkman, An Ultrastructural Study of Oocyte Growth Within the Endoderm and Entry Into the Mesoglea in Actinia fragacea (Cnidaria, Anthozoa), Journal of Morphology, vol. 178, Issue 2, pp. 155-177 (1983).

United States Patent and Trademark Office, "Non-Final Office Action", issued inU.S. Appl. No. 15/082,195, which is a divisional application of U.S. Appl. No. 14/003,509, which is a parent application of the present application, with a notification date of May 16, 2016, 24 pages.

United States Patent and Trademark Office, "Advisory Action", issued in U.S. Appl. No. 14/003,509, with a notification date of Sep. 8, 2014, 5 pages.

International Search Report received for PCT Patent Application No. PCT/JP2015/003310 dated Aug. 11, 2015, 3 pages.

European Patent Office, "Extended European Search Report," issued in European Patent Application No. 15 819 235.1, with an issuance date of Dec. 13, 2017.

\* cited by examiner

METHOD FOR SEALING SUBSTANCES, METHOD FOR DETECTING TARGET MOLECULE, ARRAY, KIT, AND TARGET MOLECULE DETECTION DEVICE

CROSS REFERENCE TO RELATED APPLICATIONS

This patent application claims the benefit of foreign priority to Japanese Patent Application No. JP 2014-140700 filed on Jul. 8, 2014, the disclosure of which is hereby incorporated by reference in its entirety. This patent application also incorporates by reference in their entireties the disclosures of: Japanese Patent Application No. JP 2011-050629 filed on Mar. 8, 2011; International Patent Application No. PCT/JP2012/055884 filed on Mar. 7, 2012, which claims the benefit of foreign priority to Japanese Patent Application No. JP 2011-050629; and U.S. application Ser. No. 14/003,509, now U.S. Pat. No. 9,329,174, having a filing or 371(c) date of Sep. 6, 2013, which is a U.S. national stage application under 35 U.S.C. § 371 of International Patent Application No. PCT/JP2012/055884.

FIELD OF THE INVENTION

The present invention relates to a method for sealing substances, a method for detecting a target molecule, an array, a kit, and a target molecule detection device.

BACKGROUND OF THE INVENTION

There has been known a single-molecule assay as a method for carrying out various assays by observing biomolecules such as proteins and nucleic acids in such a manner that the biomolecules are individually identified. In order to carry out the single-molecule assay, there have been known some methods.

Patent Literature 1 discloses a micro chamber for detecting single-molecule enzyme activity. This micro chamber includes a container part into which a liquid droplet can be sealed and which has capacity of storing a liquid droplet of up to 1000 fL (femtoliters). The container part is made of a recess provided in at least one of a first member and a second member which are bonded to each other. According to Patent Literature 1, an enzyme reaction is carried out in the liquid droplet. With such a configuration, the enzyme reaction can be performed with a high concentration of the reaction products, even if the number of molecules of the reaction products is quite small. Thus, it is possible to detect an activity of one molecule of enzyme.

Non-Patent Literature 1 discloses a method for carrying out a single-molecule enzyme assay by use of an array where a liquid droplet is covered with oil, in a femtoliter-order, and accessible directly from the outside. This array includes a hydrophilic region pattern made of a hydrophilic surface on which a hydrophobic region having a height of 17 nm is provided.

Non-Patent Literature 2 discloses a method for detecting a protein by a single-molecule Enzyme-Linked ImmunoSorbent Assay (ELISA). According to this method, a very small amount of proteins are captured by minute beads covered with protein-specific antibodies, and complexes of the beads and the proteins are fluorescence-labeled. Then, beads including the complexes are introduced into a reaction chamber by centrifugal force. Thereafter, the number of beads having captured the proteins is counted. In this manner, the proteins are quantitatively assayed.

CITATION REFERENCES

Patent Literatures

[Patent Literature 1] Japanese Patent Application Publication, Tokukai, No. 2004-309405 A

Non-Patent Literatures

[Non-Patent Literature 1] S. Sakakihara et al., Lab Chip, 2010, 10, 3355-3362
[Non-Patent Literature 2] David M Rissin et al., Nature Biotechnology: doi: 10.1038/nb

BRIEF SUMMARY OF THE INVENTION

Technical Problem

In order to detect, e.g., disease markers of low concentration for early detection of diseases, infectious diseases, and the like, there is a demand for biosensing techniques developed to have higher sensitivities. For example, in a case where one million cancer cells included in a tumor having a volume of 1 $mm^3$ secrete marker proteins (100 molecules per cell) into 5-liter blood, a concentration of the proteins in the blood is approximately 30 aM (i.e., $3*10^{-18}$ M). A technique capable of detecting target molecules of such quite low concentration is needed.

A possible method for detecting such the target molecules may be the one for detecting the target molecules by the above-mentioned single-molecule enzyme assay at a single molecule level sensitivity. Specifically, such the method is carried out by (i) sealing the target molecule specifically into a femtoliter-order liquid droplet (very small liquid droplet), (ii) linking the target molecule to a substance such as an enzyme-labeled antibody, and (iii) detecting an activity of the enzyme labeling the antibody in the above-mentioned manner. The sealing of the target molecule specifically into the very small liquid droplet may be carried out by a method using, e.g., a bead labeled with a substance such as another antibody for specifically binding to the target molecule. In this method, after the bead is bound to the target molecule, the bead is sealed into the very small solution droplet.

Incidentally, in order to efficiently detect target molecules which are contained in a solution only in a very small amount e.g., approximately 30 aM target molecules as described above, it is necessary to prepare a large number of very small liquid droplet arrays, as many as approximately one million, and to cause the arrays to capture the beads.

However, according to the method disclosed by Non-Patent Literature 2, the beads need to be introduced into arrays by strong centrifugal force, and therefore much time and efforts are required. Further, the number of arrays used in the method of Non-Patent Literature 2 is approximately fifty thousand. Therefore, the method of Non-Patent Literature 2 is quite difficult to be applied to the case requiring approximately one million arrays. Thus, with the method of Non-Patent Literature 2, it is difficult to efficiently seal a large number of beads into the arrays. Incidentally, none of Patent Literature 1 and Non-Patent Literature 1 discloses any method for solving such the problem.

In view of this, the present invention has an object to provide a technique for efficiently sealing a large number of substances, such as beads, nucleic acid, protein, virus, cells, and lipid membrane complex, into an array.

Solution to Problem

In order to attain the above object, a method of the present invention for sealing beads includes: (i) a step of introducing a hydrophilic solvent containing beads into a space between (a) a lower layer section including a plurality of receptacles each of which is capable of storing only one of the beads and which are separated from each other by a side wall having a hydrophobic upper surface and (b) an upper layer section facing a surface of the lower layer section on which surface the plurality of receptacles are provided; and (ii) a step of introducing a hydrophobic solvent into the space, the step (ii) being carried out after the step (i).

In order to attain the above object, an array of the present invention includes: a lower layer section provided with a plurality of receptacles being separated from each other by a side wall having a hydrophobic upper surface; and an upper layer section facing, via a space, a surface of the lower layer section on which surface the plurality of receptacles are provided.

In order to attain the above object, the present invention further provides the following method for sealing a substance and the like.

[1] A method for sealing a substance, including: (i) a step of introducing a first solvent containing a substance on a substrate on which a plurality of receptacles capable of storing the substance are formed separated from each other by a side wall; and (ii) a step of introducing a second solvent having a greater specific gravity than that of the first solvent onto the first solvent, the step (ii) being carried out after the step (i).

[2] The method as set forth in [1], wherein at least one of the first solvent and the second solvent contains a surfactant.

[3] The method as set forth in [2], wherein the surfactant is polyoxyethylene sorbitan monolaurate (TWEEN 20) or polyethylene glycol mono-4-octylphenyl ether (Triton X-100).

[4] The method as set forth in [2] or [3], wherein the surfactant has a concentration of 0.001% to 1%.

[5] The method as set forth in any one of [1] to [4], wherein the second solvent is at least one selected from the group consisting of saturated hydrocarbon, unsaturated hydrocarbon, aromatic hydrocarbon, silicone oil, hexafluoropropylene epoxide polymer, a polymer having a hydrofluoroether structure, perfluoropolyether, chlorotrifluoroethylene polymer, and a polymer having a perfluorocarbon structure, or is a mixture including the at least one.

[6] The method as set forth in any one of [1] to [5], wherein the first solvent is at least one selected from the group consisting of water, hydrophilic alcohol, hydrophilic ether, ketone, nitrile solvents, dimethyl sulfoxide, and N,N-dimethylformamide, or is a mixture including the at least one.

[7] The method as set forth in any one of [1] to [6], wherein the side wall has a hydrophobic upper surface.

[8] The method as set forth in any one of [1] to [7], wherein a region including the receptacles of the substrate is opened to the outside.

[9] The method as set forth in any one of [1] to [8], wherein the substance is one or more selected from beads, nucleic acid, protein, virus, cells, and lipid membrane complex.

[10] A method for detecting a target molecule, including: (i) a step of reacting beads specifically capturing target molecules with the target molecules; a step of carrying out, by use of the beads, a method recited in any one of [1] to [8], the step (ii) being carried out after the step (i); and a step of determining whether or not any one of beads having captured the target molecule is stored in each of the plurality of the receptacles, the step (iii) being carried out after the step (ii).

[11] The method as set forth in [10], wherein the beads are such beads to which molecules specifically bindable to the target molecules are bound.

Advantageous Effects of Invention

The use of the method for sealing a substance according to the present invention makes it possible to efficiently seal many substances, such as beads, nucleic acid, protein, virus, cells, and lipid membrane complex, into an array, thereby contributing to a technique by which target molecules of low concentration are detectable with high sensitivity.

BRIEF DESCRIPTION OF THE SEVERAL VIEWS OF THE DRAWING

The patent or application file contains at least one drawing executed in color. Copies of this patent or patent application publication with color drawing(s) will be provided by the Office upon request and payment of the necessary fee.

(a) through (e) of FIG. 1 are views schematically illustrating a method for sealing beads according to the present invention, and show lateral cross-sectional views of an array 1.

Figure 6:
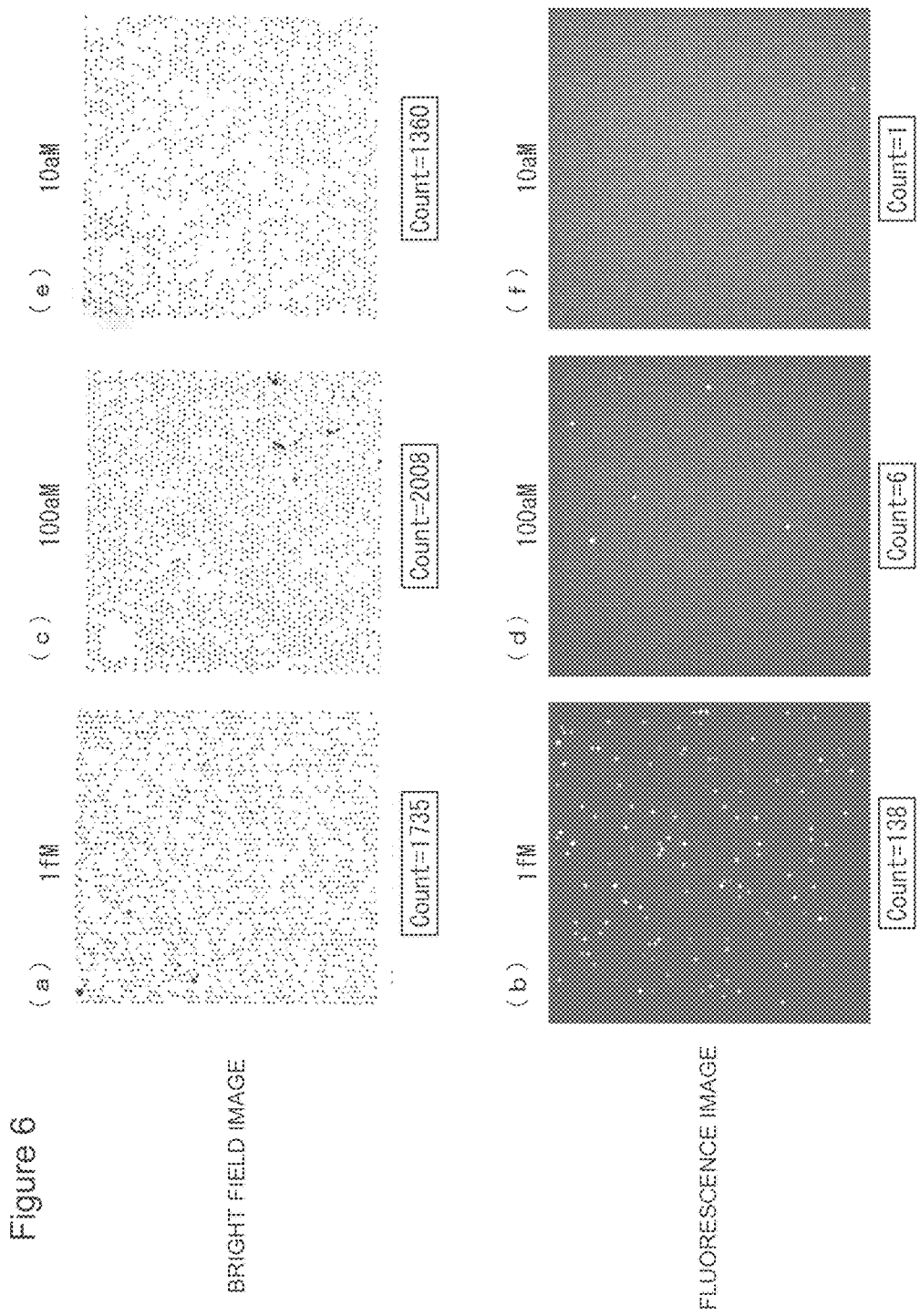

(a) through (f) of FIG. 6 show microscopic images of arrays into which beads were sealed in Example 2.

Figure 7:
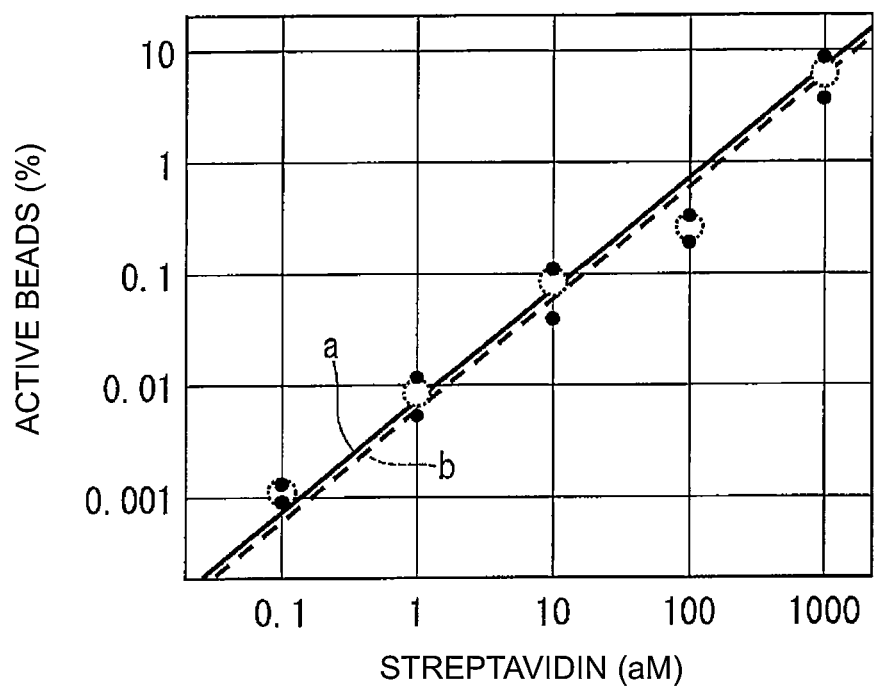

FIG. 7 shows a graph illustrating a relationship, observed in Example 2, between (i) a concentration of streptavidin and (ii) a ratio of the number of beads having captured streptavidin with respect to the number of beads stored in the array.

Figure 8:
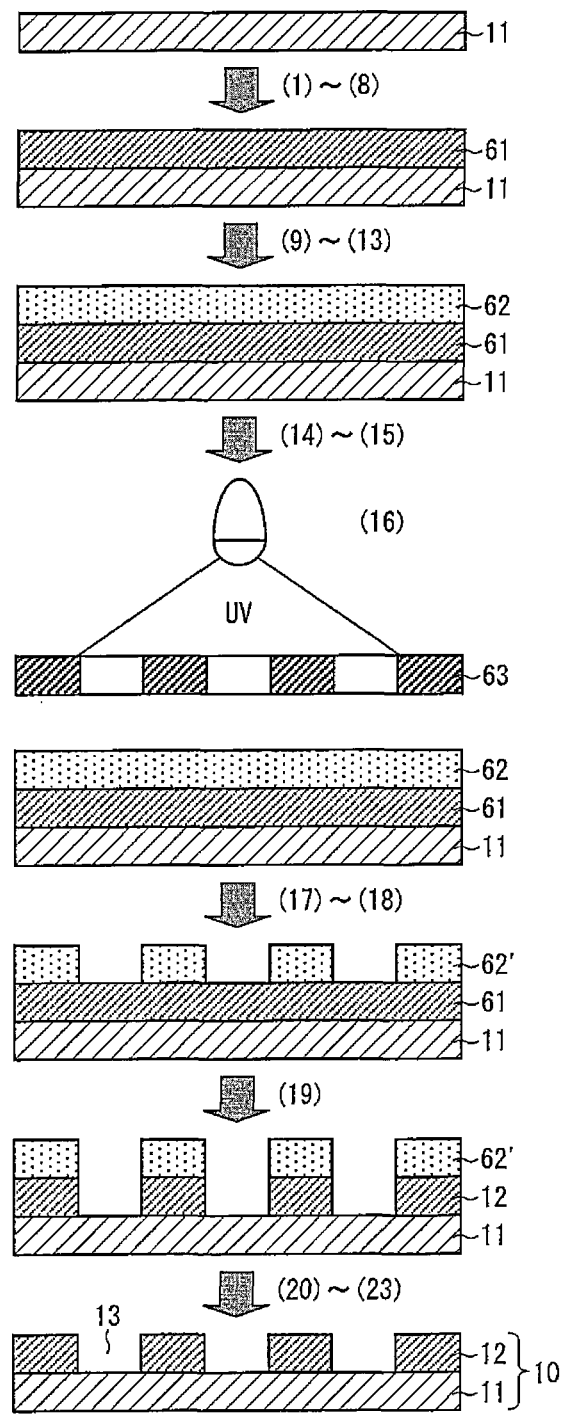

FIG. 8 is a view for explaining a method for preparing a hydrophilic-hydrophobic patterned glass according to an example of the present invention.

Figure 9:
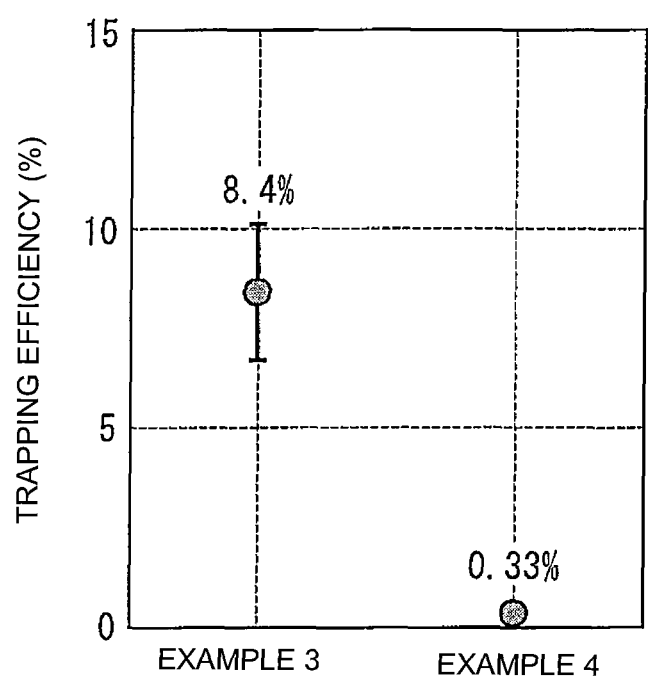

FIG. 9 is a view illustrating (i) a bead trapping efficiency found in a case involving the use of an array having a flow cell structure (Example 3) and (ii) a bead trapping efficiency found in a case involving the use of an array not having the flow cell structure (Example 4).

Figure 10A:
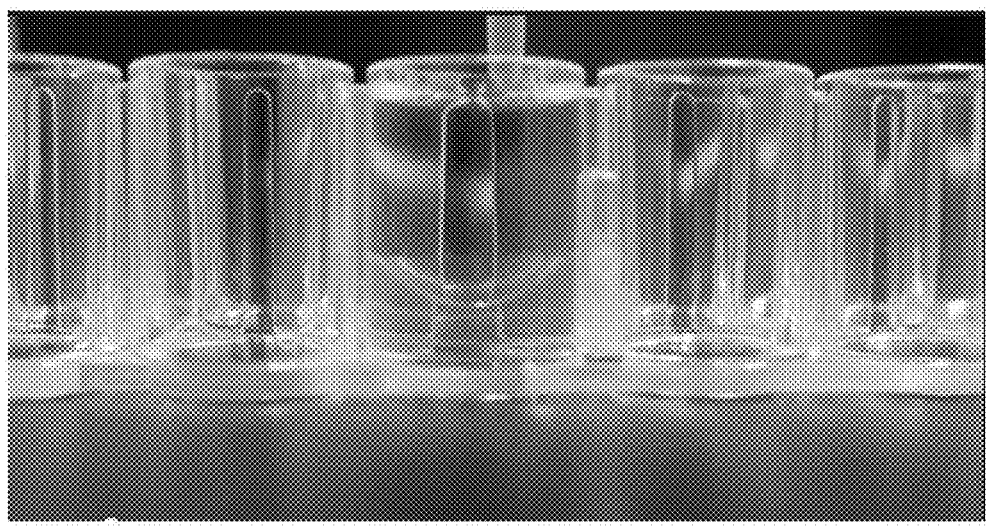

FIG. 10A is a photograph showing the appearance of the layer substitution between a beads solution and FC40 in a case involving the use of an array not having the flow cell structure.

Figure 10B:
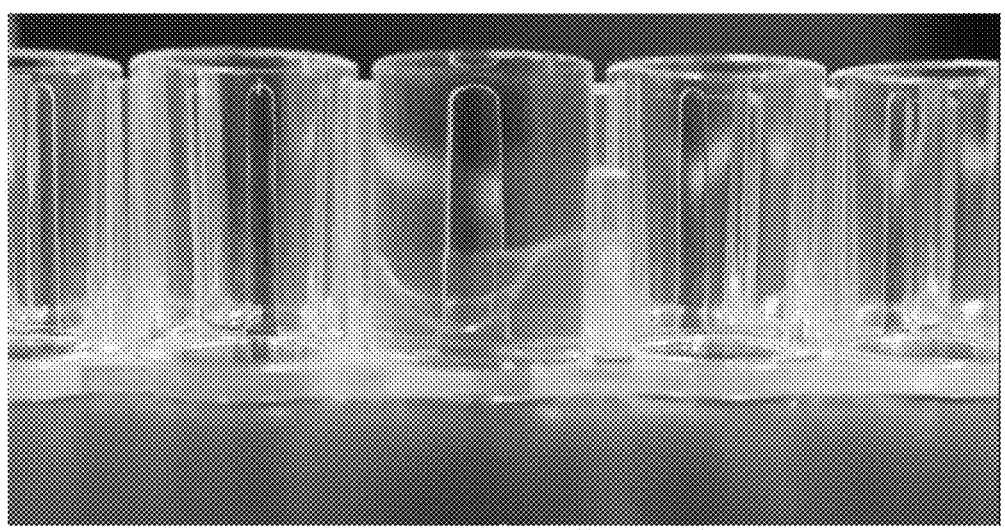

FIG. 10B is a photograph showing the appearance of the layer substitution between a beads solution and FC40 in a case involving the use of an array not having the flow cell structure.

Figure 10C:
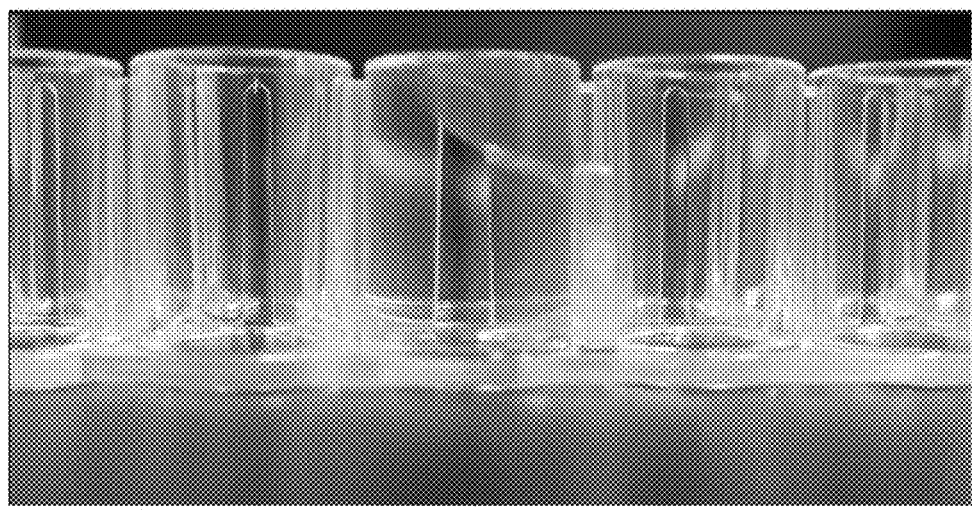

FIG. 10C is a photograph showing the appearance of the layer substitution between a beads solution and FC40 in a case involving the use of an array not having the flow cell structure.

Figure 10D:
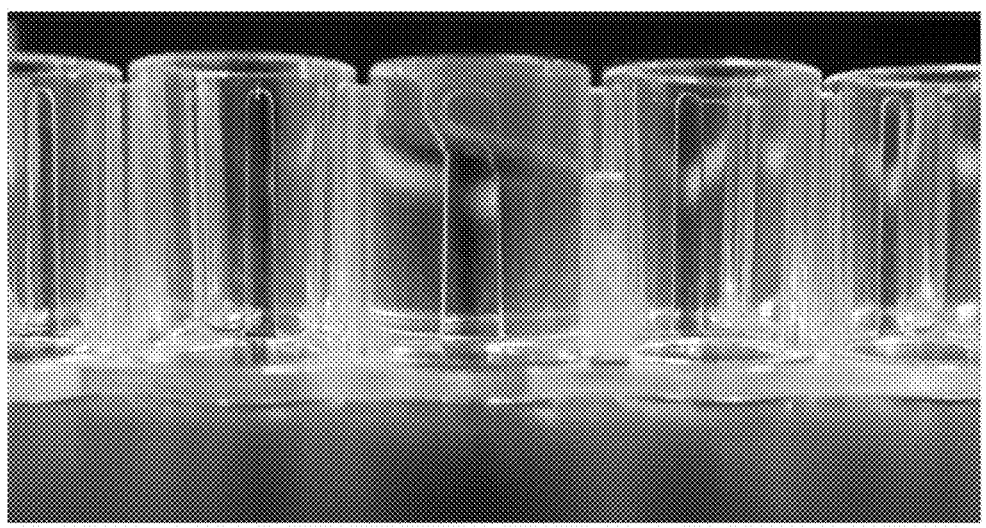

FIG. 10D is a photograph showing the appearance of the layer substitution between a beads solution and FC40 in a case involving the use of an array not having the flow cell structure.

Figure 11:
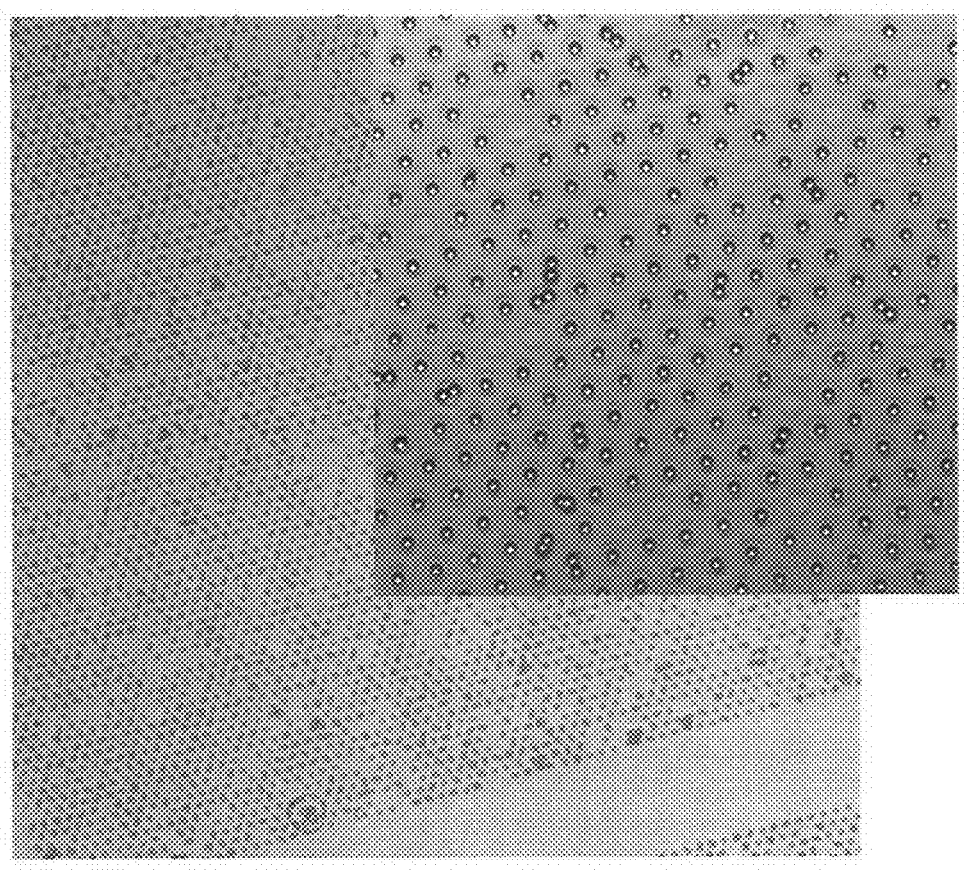

FIG. 11 is a pair of drawings showing a micrograph of a part of an array in which beads are sealed in Example 4, and its magnified image.

DETAILED DESCRIPTION OF THE INVENTION

1. First Embodiment

The following describes a first embodiment of the present invention in details.

1-1. Method for Sealing Beads

Figure 1:
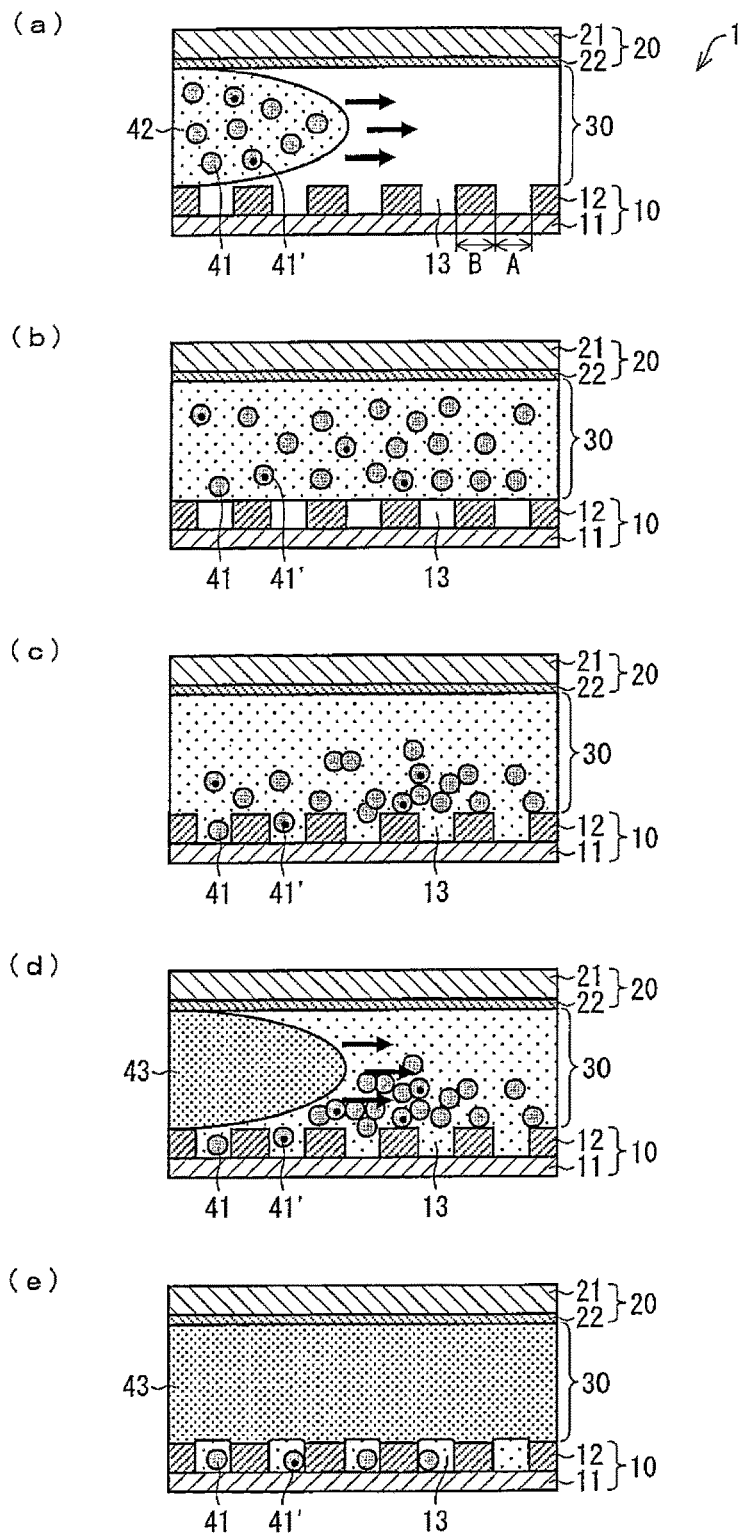

With reference to (a) through (e) of FIG. 1, the following describes a method for sealing beads according to the present embodiment. (a) through (e) of FIG. 1 are views schematically illustrating a method for sealing beads according to the present invention, and show lateral cross-sectional views of an array 1.

The present embodiment deals with a case where beads 41 and 41' are sealed into the array 1 including a lower layer section 10 and an upper layer section 20. The lower layer section 10 includes a plurality of receptacles 13 each of which is capable of storing only one of the beads 41 and 41' and which are separated from each other by a side wall 12 having a hydrophobic upper surface. Further, the upper layer section 20 faces a surface of the lower layer section 10 on which surface the receptacles 13 are provided.

Preferably, the beads have an average particle diameter of 1 µm to 4 µm. With this, the beads can be efficiently sealed into the array, and the array can achieve high density. Note that the term "average particle diameter" herein refers to a value obtained as a result of measurement of the beads by means of electron microscope observation or dynamic light scattering.

The present embodiment describes, but is not particularly limited to, a case of using beads specifically capturing target molecules. In the present embodiment, the beads to be sealed are a mixture of the beads 41, which have not captured the target molecules yet, and the beads 41', which have captured the target molecules.

For example, it is possible to use, as the beads specifically capturing the target molecules, beads being bound to a molecule for specifically capturing the target molecule. The molecule for specifically capturing the target molecule may be bound to a modification group on a surface of the bead, e.g., via a linker. For example, the present invention may be configured such that the molecule for specifically capturing the target molecule is covalently bonded to an amino group on a surface of an amino group-modified bead via a cross-linker having N-hydroxysuccinimide and/or the like.

The "target molecule" refers to a molecule which is to be detected (targeted molecule). Specifically, the "target molecule" herein refers to a molecule which is to be detected by causing the bead to capture the molecule. Examples of the target molecule encompass (i) biomolecules such as a protein, a nucleic acid, and sugar and (ii) virus particles themselves.

The molecule for specifically capturing the target molecule (hereinafter, such molecule is also referred to as a "target capturing molecule") may be chosen according to the target molecule. Examples of the target capturing molecule encompass a protein, an antibody, and a nucleic acid. Preferably, one bead is bounded to hundred thousand or more target capturing molecules. For example, in a case where the target capturing molecule is an antibody, the target capturing molecule has a dissociation constant in nM order or so. However, with the above-mentioned configuration, it is possible to cause the reaction between the beads and the target molecules with a sufficiently high concentration of the target capturing (for example, in a case where the concentration of the beads is $8*10^6$ particles/mL, the concentration of the target capturing molecules is approximately 1 nM).

The method for sealing beads according to the present embodiment includes a step of beads introduction, a step of deaeration, and a step of hydrophobic solvent introduction. Each of these steps will be described in detail below.

[Step of Beads Introduction]

The following describes the step of beads introduction with reference to (a) and (b) of FIG. 1.

The step of beads introduction is a step of introducing a hydrophilic solvent 42 containing the beads 41 and 41' into a space 30 between the lower layer section 10 and the upper layer section 20. The hydrophilic solvent 42 may be introduced into the space 30 between the lower layer section 10 and the upper layer section 20 along a direction which is in parallel with surfaces of the lower layer section 10 and the upper layer section 20, the surfaces of the lower layer section 10 and the upper layer section 20 facing each other. For example, the hydrophilic solvent 42 may be introduced into the space 30 via a through-hole (not shown) provided in at least one of the upper layer section 20 and the lower layer section 10.

Preferably used as the hydrophilic solvent 42 is, for example, at least one selected from the group consisting of water, hydrophilic alcohol, hydrophilic ether, ketone, nitrile solvents, dimethyl sulfoxide (DMSO), and N,N-dimethylformamide (DMF) or is a mixture including the at least one. Examples of hydrophilic alcohol encompass ethanol, methanol, propanol, and glycerin. Examples of hydrophilic ether encompass tetrahydrofuran, polyethylene oxide, and 1,4-dioxane. Examples of ketone encompass acetone and methyl ethyl ketone. Examples of the nitrile solvents encompass acetonitrile.

In addition to the beads 41 and 41', the hydrophilic solvent 42 may further include, e.g., a substance for specifically detecting the target molecule captured by any of the beads 41'. Such the substance may be, for example, a fluorescent substrate which liberates a fluorescent material when decomposed by a certain enzyme bound to (i) the target molecule captured by any of the beads 41' or (ii) a molecule specifically bound to the target molecule. Examples of the molecule specifically bound to the target molecule encompass a secondary antibody and a nucleic acid. Examples of the certain enzyme encompass β-galactosidase and peroxidase. Examples of the fluorescent substrate encompass fluorescein-di-β-galactopyranoside (FDG) and Amplex Red (Registered Trademark).

[Step of Deaeration]

The following describes the step of deaeration with reference to (c) of FIG. 1.

The step of deaeration is a step of deaerating the space 30 between the lower layer section 10 and the upper layer section 20, which is carried out after the step of beads introduction and before the step of hydrophobic solvent introduction. Preferably, the deaeration is carried out by, for example, a method of allowing the array 1 to stand still under reduced pressure. Specifically, the deaeration is carried out by, for example, a method of allowing the array 1 to stand still in a vacuum desiccator of approximately 0.1 atm for approximately 30 seconds.

The step of deaeration is not essential for the present invention. However, carrying out the step of deaeration removes the air in the receptacles 13, thereby making it possible to efficiently introduce into the receptacles 13 the hydrophilic solvent 42 containing the beads 41 and 41'. This enables to efficiently seal the beads 41 and 41' into the receptacles 13. Therefore, it is preferable to carry out the step of deaeration.

[Step of Hydrophobic Solvent Introduction]

The following describes the step of hydrophobic solvent introduction with reference to (d) and (e) of FIG. 1.

The step of hydrophobic solvent introduction is a step of introducing a hydrophobic solvent 43 into the space 30 between the lower layer section 10 and the upper layer section 20. The step of hydrophobic solvent introduction is carried out after the step of beads introduction, and preferably carried out after the step of deaeration.

The hydrophobic solvent 43 only needs to be a solvent that is difficult to be mixed with the hydrophilic solvent 42, which is used in the step of beads introduction. Preferably used as the hydrophobic solvent 43 is, for example, at least one selected from the group consisting of saturated hydrocarbon, unsaturated hydrocarbon, aromatic hydrocarbon, silicone oil, perfluorocarbon, halogen solvents, and hydrophobic ionic liquid or is a mixture including the at least one. Examples of saturated hydrocarbon encompass alkane and cycloalkane. Examples of alkane encompass decane and hexadecane. Examples of unsaturated hydrocarbon encompass squalene. Examples of aromatic hydrocarbon encompass benzene and toluene. Examples of perfluorocarbon encompass Fluorinert (Registered Trademark) FC40 (available from SIGMA). Examples of the halogen solvents encompass chloroform, methylene chloride, carbon dichloride and chlorobenzene. The hydrophobic ionic liquid denotes ionic liquid which is not dissociated at least in water. Examples of such the ionic liquid encompass 1-butyl-3-methylimidazolium hexafluorophosphate. The ionic liquid denotes a salt which is in the form of liquid at room temperature.

Carrying out the step of hydrophobic solvent introduction makes it possible to efficiently form, in the respective receptacles 13, droplets (liquid droplets) covered with the hydrophobic solvent 43. Also, carrying out the step of hydrophobic solvent introduction makes it possible to efficiently seal the beads 41 and 41' into the droplets so that any one of the beads 41 and 41' is stored in each of the droplets.

According to the present embodiment, the beads 41 and 41' are introduced through the space 30 between the lower layer section 10 and the upper layer section 20, thereby enabling highly-efficient sealing of any one of the beads into each of a large number of receptacles 13 which are provided in a large area (e.g., an area of 1 $cm^2$ or more).

The present embodiment enables to provide a large-area droplet array including a large number of receptacles. For example, even with an array including one million or more receptacles, it is possible to efficiently seal the beads 41 and 41' into the receptacles so that any one of the beads 41 and 41' is stored in each of the receptacles. Thus, with the present embodiment, it is possible to detect the target molecules with high sensitivity, thereby enabling to detect the target molecules of such a quite low concentration as approximately 0.1 aM.

1-2. Method for Detecting Target Molecule

Next, the following describes the method for detecting the target molecule according to the present embodiment.

The method for detecting the target molecule according to the present embodiment includes a step of reaction, a step of sealing beads, and a step of determination.

The present embodiment uses, as the beads, beads that specifically capture the target molecules. For example, each of such the beads may be the one having been bound to a molecule for specifically capturing the target molecule. Suitably used as the beads, the target molecule, and the molecule for specifically capturing the target molecule can be any of those exemplified in the descriptions for the above-mentioned method for sealing beads of the present embodiment.

The step of reaction is a step of reacting the beads with the target molecules. For example, the reaction between the beads and the target molecules can be carried out by mixing a solution containing the beads with a solution containing the target molecules.

The step of sealing beads is a step of carrying out the above-mentioned method for sealing beads by use of the beads which have been reacted with the target molecules in the step of reaction. Namely, the step of sealing beads is (i) a step including the step of beads introduction and the step of hydrophobic solvent introduction or (ii) a step including the step of beads introduction, the step of deaeration, and the step of hydrophobic solvent introduction. Note that descriptions of the step of beads introduction, the step of deaeration, and the step of hydrophobic solvent introduction are omitted here, since these steps can be carried out in the same manner as those described in the above section "Method for bead sealing".

The step of determination is a step of determining, after the step of sealing beads, whether or not each of the receptacles 13 contains any one of the beads 41' having captured the target molecules.

Suitable examples of the method of determining whether or not each of the receptacles 13 contains any one of the beads 41' having captured the target molecules encompass known molecular recognition reactions such as antigen-antibody reaction, streptavidin-biotin reaction, and complementary binding of nucleic acids. For example, this method can be a method of detecting a fluorescent material liberated from a fluorescent substrate when decomposed by a certain enzyme bound to (i) a target molecule or (ii) a molecule specifically bound to the target molecule. The detection of the fluorescent material is carried out by, for example, a method of determining a fluorescence intensity of each receptacle by use of, e.g., a fluorescence microscope or an image sensor.

In the step of determination, it is preferable to also determine whether each of the receptacles 13 contains any one of the beads 41 or any one of the beads 41'. The determination of whether each of the receptacles 13 contains any one of the beads 41 or any one of the beads 41' can be carried out by, for example, microscopic observation to determine the presence or absence of any one of the beads 41 or any one of the beads 41' in each of the receptacles 13. Alternatively, the determination of the presence or absence of any one of the beads 41 or any one of the beads 41' in each of the receptacles 13 can be carried out by a method of detecting scattered light from the beads or a method of measuring an electric potential with a field-effect transistor (FET).

After the step of determination, based on (i) the number of receptacles 13 containing the beads 41 or the beads 41' and (ii) the number of receptacles 13 containing the beads 41' having captured the target molecules, it is possible to calculate a ratio of the number of beads having captured the target molecules with respect to the total number of beads. In this manner, it is possible to quantify a concentration of the target molecules.

According to the present embodiment, it is possible to provide a large-area droplet array including a large number of receptacles; further, even with an array including one million or more receptacles, it is possible to efficiently seal the beads 41 and 41' into the receptacles. Thus, with the present embodiment, it is possible to detect the target molecules with high sensitivity, thereby enabling to detect the target molecules of such a quite low concentration as approximately 0.1 aM.

1-3. Array

Next, the following describes a configuration of the array 1 of the present embodiment with reference to (a) of FIG. 1. The array 1 may be an array used in the method for sealing beads according to the present embodiment, or may be an array used in the method for detecting the target molecule according to the present embodiment.

The array 1 includes the lower layer section 10 and the upper layer section 20.

The lower layer section 10 includes a plate-like member 11 and the side wall 12 having a hydrophobic upper surface. The lower layer section 10 includes the plurality of receptacles 13 that are separated from each other by the side wall 12.

Preferably, the plate-like member 11 has a hydrophilic surface. The term "hydrophilic surface" refers to a surface whose affinity with a hydrophilic solvent is higher than that with a hydrophobic solvent. The plate-like member 11 only needs to be made from a solid material. For example, the plate-like member 11 can be made from glass, silicon, or a polymer resin.

The side wall 12 is a structure that is provided on a surface of the plate-like member 11, preferably on the hydrophilic surface of the plate-like member 11, and is configured to separate the plurality of receptacles 13 from each other. The side wall 12 has the hydrophobic upper surface. The term "hydrophobic" herein is used as a synonym for "lipophilic", and denotes a nature whose affinity with a hydrophobic solvent is higher than that with a hydrophilic solvent.

Note that the side wall 12 needs to be configured such that its upper surface, i.e., its surface facing the upper layer section 20, is hydrophobic. Whereas, a lateral surface of the side wall 12, i.e., an inner wall of each of the receptacles 13, may be either hydrophobic or hydrophilic.

For example, the side wall 12 may be made of a hydrophilic structure and a hydrophobic layer which is formed on an upper surface of the hydrophilic structure. The hydrophilic structure may be made from, e.g., glass, silicon, or a polymer resin. The hydrophobic layer may be made from, e.g., a water repellent resin or a fluorocarbon polymer resin. Examples of the fluorocarbon polymer resin encompass amorphous fluorocarbon resin. The amorphous fluorocarbon resin is preferably used, because the amorphous fluorocarbon resin has a high hydrophobic property and has a low toxicity to a biological sample.

Preferable examples of the amorphous fluorocarbon resin encompass at least one selected from CYTOP (Registered Trademark), TEFLON (Registered Trademark) AF2400, and TEFLON (Registered Trademark) AF1600. Among those, CYTOP (Registered Trademark) is most preferable, since it is easy to be microfabricated. CYTOP (Registered Trademark) has the following general formula:

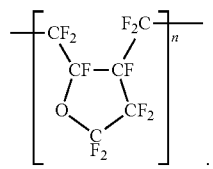

TEFLON (Registered Trademark) AF2400 and TEFLON (Registered Trademark) AF1600 are poly[4,5-difluoro-2,2-bis(trifluoromethyl)-1,3-dioxole-co-tetrafluoroethylene], which has the following general formula:

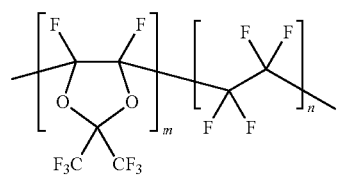

In AF2400, the dioxole component is 87 mol %, and in AF1600, it is 65 mol %.

Alternatively, the side wall 12 may be made from a hydrophobic material. For example, the side wall 12 may be made from a fluorocarbon polymer resin or a paraxylene polymer resin. Examples of the fluorocarbon polymer resin encompass an amorphous fluorocarbon resin. Preferably used as the amorphous fluorocarbon resin is any of those exemplified above.

The side wall 12 only needs to have such a configuration that the plurality of receptacles 13 are provided on the plate-like member 11. For example, the side wall 12 may be a plate-like structure parts of which corresponding to the receptacles 13 are holes.

A height (i.e., a thickness in a vertical direction) of the side wall 12 measured from the surface of the plate-like member 11 only needs to be designed so that one of the beads 41 and 41' contained in one of the receptacles 13 would not be discharged therefrom during the later-described step of hydrophobic solvent introduction. For example, the height of the side wall 12 may be designed so that most part of, preferably the whole part of, one of the beads 41 and 41' contained in one of the receptacles 13 is positioned lower than the upper surface of the side wall 12.

In order to efficiently store the beads 41 and 41' in the receptacles 13, the height of the side wall 12 is preferably equal to or greater than the average particle diameter of the beads 41 and 41'. Further, in order that only one of the beads 41 and 41' is stored in one of the receptacles 13, the height of the side wall 12 is preferably equal to or smaller than 1.5 times the average particle diameter of the beads 41 and 41'.

Each of the plurality of receptacles 13 is a recess capable of storing only one of the beads 41 and 41', and the plurality of receptacles 13 are separated from each other by the side wall 12. Each of the receptacles 13 has a bottom surface which is a part of the surface of the plate-like member 11, and the bottom surface is hydrophilic.

The receptacles 13 can have any shape or size, as long as the shape or size allows each of the receptacles 13 to store only one of the beads 41 and 41' therein. A region surrounded by the bottom surface and the lateral surface of each of the receptacles 13 may be shaped in, e.g., a circular cylinder or a rectangular column.

A width "A" of each of the receptacles 13 in a horizontal direction (e.g., in a case where a cross section of each receptacle 13 when seen in the horizontal direction is shaped in a circle, the width "A" is a diameter of the circle; in a case where the cross section of each receptacle 13 when seen in the horizontal direction is shaped in a square, the width "A" is a length of one side of the square) only needs to be larger than the average particle diameter of the beads 41 and 41'. Preferably, the width "A" is 1.5 to 2 times larger than the average particle diameter of the beads 41 and 41', for example. In the present embodiment, each of the receptacles 13 has a depth equal to the height of the side wall 12. In order to efficiently store the beads in the receptacles, the depth of each of the receptacles of the present invention is preferably equal to or greater than the average particle diameter of the beads. Further, in order that only one of the beads is stored in one of the receptacles, the depth of each of the receptacles of the present invention is preferably equal to or smaller than 1.5 times the average particle diameter of the beads.

According to the present embodiment, each of the receptacles 13 has the hydrophilic bottom surface, and the side wall 12 has the hydrophobic upper surface. This makes it possible to efficiently introduce the hydrophilic solvent 42 containing the beads 41 and 41' into the receptacles 13 in the later-described step of beads introduction, and to prevent the hydrophobic solvent 43 from entering the receptacles 13 in the later-described step of hydrophobic solvent introduction. With this, the receptacles 13 storing the liquid droplets containing the beads 41 and 41' can be hermetically sealed with the hydrophobic solvent in an efficient manner.

The upper layer section 20 includes a plate-like member 21 and a hydrophobic layer 22. The hydrophobic layer 22 is provided on a surface of the plate-like member 21 which surface faces the lower layer section 10. The plate-like member 21 is made from, e.g., glass, silicon, or a polymer resin. The hydrophobic layer 22 is made from, e.g., a water repellent resin or a fluorocarbon polymer resin. Examples of the fluorocarbon polymer resin encompass amorphous fluorocarbon resin.

The upper layer section 20 faces, via the space 30, the surface of the lower layer section 10 on which surface the receptacles 13 are provided. Namely, the space 30 exists between the side wall 12 and the hydrophobic layer 22. The space 30 serves as a flow path. Thus, the array 1 is configured to have a flow cell structure.

The space 30 can be used as the flow path for allowing a fluid to flow between the lower layer section 10 and the upper layer section 20 in a direction in parallel with the surfaces of the lower layer section 10 and the upper layer section 20, the surfaces of the lower layer section 10 and the upper layer section 20 facing each other.

A distance between (i) the upper surface of the side wall 12 and (ii) the hydrophobic layer 22 or the plate-like member 21, i.e., a width of the space 30 in the vertical direction only needs to be larger than the average particle diameter of the beads 41 and 41', and is preferably 10 μm to 150 μm.

The lower layer section 10 or the upper layer section 20 may be provided with the through-hole (not shown) through which the fluid is introduced into the space 30. For example, the lower layer section 10 may have a region provided with the receptacles 13 and a region provided with no receptacles 13. Further, the lower layer section 10 may have the through-hole in the region provided with no receptacles 13; alternatively, the upper layer section 20 may have the through-hole in a region facing the region of the lower layer section 10 provided with no receptacles 13.

According to the present embodiment, an upper side of the space 30 corresponds to the surface of the hydrophobic layer 22, and a lower side of the space 30 corresponds to the upper surface of the side wall 12 and the receptacles 13. Thus, except for parts of the space 30 corresponding to the bottom surfaces of the receptacles 13, the entire space 30 has a hydrophobic property. This configuration makes it possible to efficiently introduce the hydrophilic solvent 42 containing the beads 41 and 41' into the receptacles 13 in the above-described step of beads introduction. Further, this configuration prevents the hydrophobic solvent 43 from entering the receptacles 13 in the above-described step of hydrophobic solvent introduction. Thus, by introducing the hydrophobic solvent 43 into the space 30, it is possible to efficiently form, in each of the receptacles 13, a droplet into which any one of the beads 41 and 41' is sealed.

The array 1 of the present embodiment may be, for example, an array including one million or more receptacles. Even with the array having such a large area, the use of the method for sealing beads of the present embodiment or the method for detecting the target molecule of the present embodiment makes it possible to efficiently seal the beads into the receptacles so that any one of the beads is stored in each of the receptacles. Thus, according to the present embodiment, it is possible to detect the target molecules with high sensitivity, thereby enabling to provide an array allowing detection of target molecules of such a quite low concentration as approximately 0.1 aM.

2. Second Embodiment

The following describes a second embodiment of the present invention in details.

In the method for sealing a substance according to the present invention, the substance sealed in receptacles provided on a substrate may be beads, nucleic acid, protein, virus, cells, lipid membrane complex, or the like; however, the following embodiment will be described using beads as an example.

2-1. Method for Sealing Beads

Figure 2:
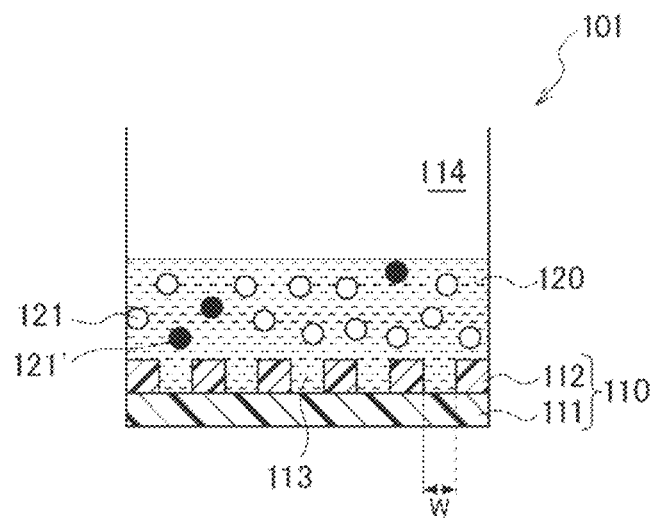
FIG. 2 is a series of views schematically illustrating the procedure of the method for sealing a substance according to the present invention, which show lateral cross-sectional views of an array 101.
Figure 2:
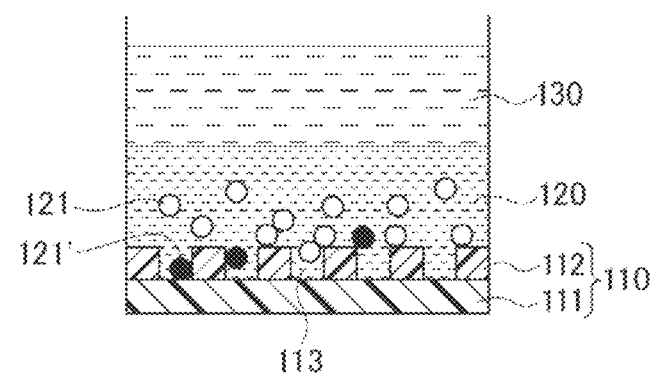
Figure 2:
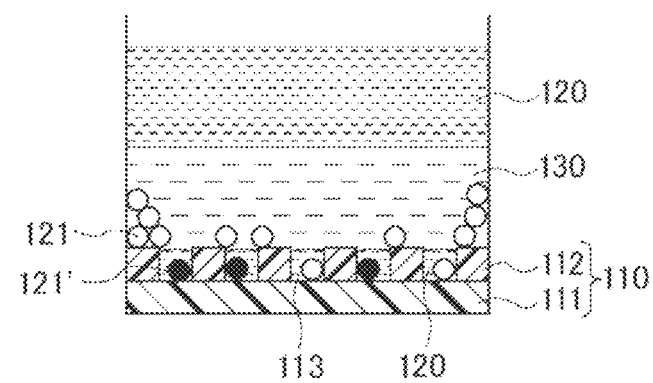

With reference to FIG. 2, the following describes a method for sealing beads according to the present embodiment. FIG. 2 is a series of views schematically illustrating the procedure of the method for sealing beads according to the present embodiment, which show lateral cross-sectional views of an array 101.

The present embodiment deals with a case will be described where beads 121 and 121' are sealed into the array 101 including a substrate 110. The substrate 110 includes a plurality of receptacles 113 each of which is capable of storing only one of the beads 121 and 121' and which are separated from each other by a side wall 112 having a hydrophobic upper surface.

Here, for the purpose of the present invention (including the first embodiment), "bead" is used synonymously with "particle" and is a technical term commonly used in the art. The shape of the bead is not particularly limited; however, it is typically spherical. The material of the bead is also not particularly limited and may be glass, silica gel, polystyrene, polypropylene, membrane, magnetic material, or the like. Specific examples of the material include cellulose, cellulose derivatives, acrylic resin, glass, silica gel, polystyrene, gelatin, polyvinylpyrrolidone, copolymers of vinyl and acrylamide, polystyrenes crosslinked with divinylbenzene and the like, polyacrylamide, latex gel, polystyrene dextran, rubber, silicon, plastics, nitrocellulose, cellulose, natural sponge, silica gel, glass, metal plastics, cellulose, cross-linked dextran (Sephadex (Registered Trademark)), and agarose gel (Sepharose (Registered Trademark)). The beads may be porous. The beads preferably have an average particle diameter of 5 µm or less, for example, approximately 1 µm to 4 µm. With this, the beads can be efficiently sealed into the array, and the array can achieve high density. Note that the term "average particle diameter" herein refers to a value obtained as a result of measurement of the beads by means of electron microscope observation or dynamic light scattering.

The present embodiment describes, but is not particularly limited to, a case of using beads specifically capturing target molecules. In the present embodiment, the beads to be sealed are a mixture of the beads 121, which have not captured the target molecules yet, and the beads 121', which have captured the target molecules.

For example, it is possible to use, as the beads specifically capturing the target molecules, beads being bound to a molecule for specifically capturing the target molecule. The molecule for specifically capturing the target molecule may be bound to a modification group on a surface of the bead, e.g., via a linker. For example, the present invention may be configured such that the molecule for specifically capturing the target molecule is covalently bonded to an amino group on a surface of an amino group-modified bead via a cross-linker having N-hydroxysuccinimide and/or the like.

The "target molecule" refers to a molecule which is to be detected (targeted molecule). Specifically, the "target molecule" herein refers to a molecule which is to be detected by causing the bead to capture the molecule. Examples of the target molecule encompass (i) biomolecules, such as a protein, a nucleic acid, and sugar, and (ii) virus particles themselves.

The molecule for specifically capturing a target molecule (hereinafter such molecule is also referred to as a "target capturing molecule") may be chosen according to the target molecule. Examples of the target capturing molecule encompass a protein, an antibody, and a nucleic acid. Preferably, one bead is bounded to hundred thousand or more target capturing molecules. For example, in a case where the target capturing molecule is an antibody, the target capturing molecule has a dissociation constant in nM order or so. However, with the above-mentioned configuration, it is possible to cause the reaction between the beads and the target molecules with a sufficiently high concentration of the target capturing (for example, in a case where the concentration of the beads is $8*10^6$ particles/mL, the concentration of the target capturing molecules is approximately 1 nM).

The method for sealing beads according to the present embodiment includes a step of beads introduction, a step of deaeration, and a step of beads storing. Each of these steps will be described in detail below.

[Step of Beads Introduction]

The following describes the step of beads introduction with reference to FIG. 2(A).

The step of beads introduction is a step of introducing a first solvent 120 containing the beads 121 and 121' onto the substrate 110. The method for introducing the first solvent 120 is not particularly limited; however, a method can be adopted which involves using a region 114 including the receptacles 113 of the substrate 110 as an opened well which is opened to the outside to introduce the first solvent 120 from the opening into the well.

The first solvent 120 is preferably a hydrophilic solvent; preferably used as it is, for example, at least one selected from the group consisting of water, hydrophilic alcohol, hydrophilic ether, ketone, nitrile solvents, dimethyl sulfoxide (DMSO), and N,N-dimethylformamide (DMF) or is a mixture including the at least one. Examples of hydrophilic alcohol encompass ethanol, methanol, propanol, and glycerin. Examples of hydrophilic ether encompass tetrahydrofuran, polyethylene oxide, and 1,4-dioxane. Examples of ketones encompass acetone and methyl ethyl ketone. Examples of nitrile solvents encompass acetonitrile.

The first solvent 120 preferably contains a surfactant. In the step of beads storing to be described next, a second solvent 130 having a greater specific gravity than that of the first solvent 120 is introduced onto the first solvent 120, followed by performing substitution based on the difference in specific gravity between the first solvent 120 and the second solvent 130 to move the second solvent 130 to the lower layer of the first solvent 120 (described later for details). On this occasion, a surfactant can be added to the first solvent 120 and/or the second solvent 130 to promote the substitution between the first solvent 120 and the second solvent 130.

The surfactant is not particularly limited; however, examples thereof encompass TWEEN 20 (CAS No. 9005-64-5, polyoxyethylene sorbitan monolaurate) and Triton X-100 (CAS No. 9002-93-1, general name: polyethylene glycol mono-4-octylphenyl ether (n≈10)). The concentration (% by weight) of the surfactant added to the first solvent 120 is not particularly limited; however, it is, for example, 0.001 to 1%, preferably 0.01 to 0.1%, more preferably 0.01 to 0.05%.

In addition, an anionic surfactant, a cationic surfactant, a nonionic surfactant, a zwitterionic surfactant, a surfactant derived from nature, or the like can be widely used as the surfactant.

The anionic surfactant is classified, for example, into a carboxylic type, a sulfate type, a sulfonic type, and a phosphate type. Specific examples thereof encompass sodium dodecyl sulfate, sodium laurate, sodium α-sulfo fatty acid methyl ester, sodium dodecylbenzenesulfonate, and sodium dodecylethoxylate sulfate; among these, sodium dodecylbenzenesulfonate is preferably used.

The cationic surfactant is classified, for example, into a quaternary ammonium salt type, an alkylamine type, and a heterocyclic amine type. Specific examples thereof encompass stearyltrimethylammonium chloride, distearyldimethylammonium chloride, didecyldimethylammonium chloride, cetyltripyridinium chloride, and dodecyldimethylbenzylammonium chloride.

Examples of the nonionic surfactant encompass polyoxyethylene alkyl ethers, polyoxyethylene hydrogenated castor oils, polyoxyethylene mono fatty acid esters, polyoxyethylene sorbitan mono fatty acid esters, sucrose fatty acid esters, polyglyceryl fatty acid esters, alkyl polyglucosides, and N-methylalkyl glucamides. Among those, preferred are nonionic surfactants available under the names of Triton X (Triton X-100, and the like), Pluronic (Registered Trademark) (Pluronic F-123, F-68, and the like), Tween (Tween 20, 40, 60, 65, 80, 85, and the like), Brij (Registered Trademark) (Brij 35, 58, 98, and the like), and Span (Span 20, 40, 60, 80, 83, and 85) in addition to dodecyl alcohol ethoxylate, nonylphenol ethoxylate, and lauroyl diethanol amide.

Examples of the zwitterionic surfactant encompass lauryldimethyl aminoacetic acid betaine, dodecylaminomethyldimethylsulfopropyl betaine, and 3-(tetradecyldimethylaminio)propane-1-sulfonate; however, preferred examples thereof used encompass 3-[(3-cholamidopropyl)dimethylammonio]-1-propane sulfonate (CHAPS) and 3-[(3-cholamidopropyl)dimethylammonio]-2-hydroxy-1-propane sulfonate (CHAPSO).

The surfactant derived from nature is preferably, for example, lecithin or saponin. Among compounds called lecithin, preferred are specifically phosphatidylcholine, phosphatidylethanolamine, phosphatidylinositol, phosphatidylserine, phosphatidic acid, and phosphatidylglycerol. Quillaja saponin is preferable as saponin.

In addition to the beads 121 and 121', the first solvent 120 may further include, e.g., a substance for specifically detecting the target molecule captured by any of the beads 121'. Such the substance may be, for example, a fluorescent substrate which liberates a fluorescent material when decomposed by a certain enzyme bound to (i) the target molecule captured by any of the beads 121' or (ii) a molecule specifically bound to the target molecule. Examples of the molecule specifically bound to the target molecule encompass a secondary antibody and a nucleic acid. Examples of the certain enzyme encompass β-galactosidase and peroxidase. Examples of the fluorescent substrate encompass fluorescein-di-β-galactopyranoside (FDG) and Amplex Red (Registered Trademark).

[Step of Beads Storing]

The following describes the step of beads storing with reference to FIG. 2(B) and FIG. 2(C).

The step of beads storing is a step of introducing the second solvent 130 having a greater specific gravity than that of the first solvent 120 onto the first solvent 120. The method for introducing the second solvent 130 is not particularly limited; however, a method can be adopted which involves using the region 114 including the receptacles 113 of the substrate 110 as an opened well which is opened to the outside to introduce the second solvent 130 from the opening into the well. On this occasion, the second solvent 130 is preferably introduced so that the layer of the second solvent 130 is laminated on the layer of the first solvent 120 as shown in FIG. 2(B).

The second solvent 130 may be a solvent having a greater specific gravity than that of the first solvent 120 used in the step of beads introduction; however, it is preferably one not compatibilized with the first solvent 120. The second solvent 130 may also contain a surfactant, like the first solvent 120.

Such the second solvent 130 is preferably a hydrophobic solvent; preferably used as it is, for example, at least one selected from the group consisting of saturated hydrocarbon, unsaturated hydrocarbon, aromatic hydrocarbon, silicone oil, hexafluoropropylene epoxide polymer, a polymer having a hydrofluoroether structure, perfluoropolyether, chlorotrifluoroethylene polymer, and a polymer having a perfluorocarbon structure, or is a mixture including the at least one. Examples of saturated hydrocarbons encompass alkanes and cycloalkanes. Examples of alkanes encompass decane and hexadecane. Examples of unsaturated hydrocarbons encompass squalene. Examples of aromatic hydrocarbons encompass benzene and toluene. Examples of hexafluoropropylene epoxide polymers encompass Krytox 143 (from DuPont Co., Ltd.) and Krytox GPL (from DuPont Co., Ltd.). Examples of the polymer having a hydrofluoroether structure encompass Asahiklin AE3000 (from Asahi Glass Co., Ltd.) and Novec 7000 (from Sumitomo 3M Co., Ltd.). Examples of the polymer having a perfluorocarbon structure encompass Fluorinert FC-40 and Fluorinert FC-43 (from Sumitomo 3M Co., Ltd.).

The second solvent 130 introduced and laminated onto the first solvent 120 has a greater specific gravity than that of the first solvent 120 and thus moves down below the first solvent 120. Specifically, the substitution between the first solvent 120 and the second solvent 130 takes place and thereby the state in which the upper layer is the second solvent 130 with the lower layer being the first solvent 120 (see FIG. 2(B)) becomes a state in which the upper layer is the first solvent 120 with the lower layer being the second solvent 130 (see FIG. 2(C)). Then, as the second solvent 130 moves downward, the beads 121 and 121' contained in the first solvent 120 are also precipitated downward and stored in the respective receptacles 113 (see FIG. 2(C)). As a result, the beads can be sealed with high efficiency into each of a large number of receptacles 113 which are provided on the substrate 110. To prevent the first solvent 120 and the second solvent from being intermingled with each other, it is preferable to use a hydrophilic solvent as the first solvent 120 and a hydrophobic solvent as the second solvent 130. In this case, droplets (liquid droplets of the first solvent 120) covered by the second solvent 130 are efficiently formed in the respective receptacles 113.

Here, preferred examples of the first solvent 120 and the second solvent 130 used in the bead sealing method according to the present embodiment are as in "Table 1" and "Table 2".

TABLE 1

| First solvent | Density |
| --- | --- |
| water | 1.000 g/mL at 3.98° C. (lit.) |
| methanol | 0.791 g/mL at 25° C. (lit.) |
| ethanol | 0.789 g/mL at 25° C. (lit.) |
| 1-propanol | 0.804 g/mL at 25° C. (lit.) |
| 2-propanol | 0.785 g/mL at 25° C. (lit.) |
| 1-butanol | 0.81 g/mL at 25° C. (lit.) |
| N,N-dimethylformamide | 0.944 g/mL (lit.) |
| acetonitrile | 0.786 g/mL at 25° C. (lit.) |
| acetone | 0.791 g/mL at 25° C. (lit.) |
| tetrahydrofuran | 0.889 g/mL at 25° C. (lit.) |

TABLE 2

| Second solvent | Density |
| --- | --- |
| PF-5052 | 1.700 g/mL at 25° C. |
| Fluorinert FC-72 | 1.680 g/mL at 25° C. |
| Fluorinert FC-770 | 1.790 g/mL at 25° C. |
| Fluorinert FC-3283 | 1.830 g/mL at 25° C. |
| Fluorinert FC-40 | 1.870 g/mL at 25° C. |
| Fluorinert FC-43 | 1.880 g/mL at 25° C. |
| chloroform | 1.492 g/mL at 25° C. (lit.) |
| Asahiklin AE-3000 | 1.470 g/mL at 25° C. |
| Novec 7000 | 1.400 g/mL |
| Novec 7100 | 1.520 g/mL |
| Novec 7200 | 1.430 g/mL |
| Novec 7300 | 1.660 g/mL |
| Krytox GPL-100 | 1.87 g/mL at 0° C. |
| Krytox GPL-101 | 1.89 g/mL at 0° C. |
| Krytox GPL-102 | 1.91 g/mL at 0° C. |
| Krytox GPL-103 | 1.92 g/mL at 0° C. |
| Krytox GPL-104 | 1.93 g/mL at 0° C. |
| Krytox GPL-105 | 1.94 g/mL at 0° C. |
| Krytox GPL-106 | 1.95 g/mL at 0° C. |
| Krytox GPL-107 | 1.95 g/mL at 0° C. |

In the step of beads storing, when magnetic beads are used as the beads 121 and 121', a magnetic means may be used to promote the movement of the beads into the receptacles 113. The first solvent 120 containing the beads 121 and 121' is introduced into the region 114 including the receptacles 113 in the step of beads introduction, followed by applying an external magnetic field to the beads 121 and 121' before or after introducing the second solvent 130 onto the first solvent 120 in the step. This can promote the movement of the beads 121 and 121' into the receptacles 113 by causing force towards the receptacles 113 to act on the beads 121 and 121'. The application of the magnetic field may be carried out, for example, by causing a magnet to near the opposite side of the side on which the receptacles 113 of the substrate 110 are provided (the bottom face side of the array 101).

The present embodiment enables to provide a large-area array including a large number of receptacles. For example, even with an array including one million or more receptacles, it is possible to efficiently seal the bead 121 or 121' into the receptacles so that any one of the beads 121 and 121' is stored in each of the receptacles. Thus, with the present embodiment, it is possible to detect the target molecules with high sensitivity, thereby enabling to detect the target molecules of such a quite low concentration as approximately 10 aM.

[Step of Deaeration]

The region 114 including the receptacles 113 of the substrate 110 may be made into an upper opened space as described above; however, when the region 114 is made into a closed space, a step of deaerating the inside of the region 114 may be carried out between the step of beads introduction and the step of beads storing. Preferably, the deaeration is carried out by, for example, a method of allowing the array 101 to stand still under reduced pressure. Specifically, the deaeration is carried out by, for example, a method of allowing the array 101 to stand still in a vacuum desiccator of approximately 0.1 atm for approximately 30 seconds.

The step of deaeration is not essential for the present invention. However, carrying out the step of deaeration removes the air in the receptacles 113, thereby making it possible to efficiently introduce into the receptacles 113 the beads 121 and 121'.

2-2. Method for Detecting Target Molecule

Next, the following describes the method for detecting the target molecule according to the present embodiment. The method for detecting a target molecule according to the present embodiment includes a step of reaction, a step of sealing beads, and a step of determination.

The present embodiment uses, as the beads, beads that specifically capture the target molecules. For example, each of such the beads may be the one having been bound to a molecule for specifically capturing the target molecule. Suitably used as the beads, the target molecule, and the molecule for specifically capturing the target molecule can be any of those exemplified in the above descriptions for the method for sealing beads.

The step of reaction is a step of reacting the beads with the target molecules. For example, the reaction between the beads and the target molecules can be carried out by mixing a solution containing the beads with a solution containing the target molecules.

The step of sealing beads is a step of carrying out the above-mentioned method for sealing beads by use of the beads which have been reacted with the target molecules in the step of reaction. Namely, the step of sealing beads is a step including the step of beads introduction and the step of beads storing, or a step including the step of beads introduction, the step of deaeration, and the step of beads storing. Note that descriptions of the step of beads introduction, the step of deaeration, and the step of beads storing are omitted here, since these steps can be carried out in the same manner as those described in the above section "Method for Sealing Beads".

The step of determination is a step of determining, after the step of sealing beads, whether or not each of the receptacles 113 contains any one of the beads 121' having captured the target molecules.

Suitable examples of the method of determining whether or not each of the receptacles 113 contains any one of the beads 121' having captured the target molecules encompass known molecular recognition reactions such as antigen-antibody reaction, streptavidin-biotin reaction, or complementary binding of nucleic acids. For example, this method can be a method of detecting a fluorescent material liberated from a fluorescent substrate when decomposed by a certain enzyme bound to (i) a target molecule or (ii) a molecule specifically bound to the target molecule. The detection of the fluorescent material is carried out by, for example, a method of determining a fluorescence intensity of each receptacle by use of, e.g., a fluorescence microscope or an image sensor.

In the step of determination, it is preferable to also determine whether each of the receptacles 113 contains any one of the beads 121 or any one of the beads 121'. The determination of whether each of the receptacles 113 contains any one of the beads 121 or any one of the beads 121' can be carried out by, for example, microscopic observation to determine the presence or absence of any one of the beads 121 or any one of the beads 121' in each of the receptacles 113. Alternatively, the determination of the presence or absence of any one of the beads 121 or any one of the beads 121' in each of the receptacles 113 can be carried out by a method of detecting scattered light from the beads or a method of measuring an electric potential with a field-effect transistor (FET).

After the step of determination, based on (i) the number of receptacles 113 containing the beads 121 or the beads 121', and (ii) the number of receptacles 113 containing the beads 121' having captured the target molecules, it is possible to calculate a ratio of the number of beads having captured the target molecules with respect to the total number of beads. In this manner, it is possible to quantify a concentration of the target molecules.

According to the present embodiment, it is possible to provide a large-area array including a large number of receptacles; further, even with an array including one million or more receptacles, it is possible to efficiently seal the beads 121 or 121' into each of the receptacles. Thus, with the present embodiment, it is possible to detect the target molecules with high sensitivity, thereby enabling to detect the target molecules of such a quite low concentration as approximately 10 aM.

2-3. Array

Next, the following describes a configuration of the array 101 with reference to FIG. 2.

In the array 101, the substrate 110 includes a plate-like member 111 and the side wall 112 having a hydrophobic upper surface. The substrate 110 includes the plurality of receptacles 113 that are separated from each other by the side wall 112.

Preferably, the plate-like member 111 has a hydrophilic surface. The term "hydrophilic surface" refers to a surface whose affinity with a hydrophilic solvent is higher than that with a hydrophobic solvent. The plate-like member 111 may only needs to be made from a solid material. For example, the plate-like member 111 can be made from glass, silicon, or a polymer resin.

The side wall 112 is provided on the surface, preferably on the hydrophilic surface, of the plate-like member 111 and, separates the plurality of receptacles 113. The side wall 112 has the hydrophobic upper surface. The term "Hydrophobic" herein is used as a synonym for "lipophilic", and denotes a nature whose affinity with a hydrophobic solvent is higher than that with a hydrophilic solvent.

Note that the upper surface of the side wall 112 is preferably hydrophobic and the lateral surface thereof, i.e., an inner wall of each of the receptacles 113, may be either hydrophobic or hydrophilic.

For example, the side wall 112 may be made of a hydrophilic structure and a hydrophobic layer which is formed on an upper surface thereof. The hydrophilic structure may be made from, e.g., glass, silicon, or a polymer resin. The hydrophobic layer may be made from, e.g., a water repellent resin or a fluorocarbon polymer resin. Examples of the fluorocarbon polymer resin encompass amorphous fluorocarbon resin. The amorphous fluorocarbon resin is preferably used because of having a high hydrophobic property and having a low toxicity to a biological sample.

Preferable examples of the amorphous fluorocarbon resin encompass at least one selected from CYTOP (Registered Trademark), TEFLON (Registered Trademark) AF2400, and TEFLON (Registered Trademark) AF1600. Among those, CYTOP (Registered Trademark) is most preferable because it is easy to be microfabricated.

Alternatively, the side wall 112 may be made from a hydrophobic material. For example, the side wall 112 may be made from a fluorocarbon polymer resin or a paraxylene polymer resin. Examples of the fluorocarbon polymer resin encompass an amorphous fluorocarbon resin. Preferably used as the amorphous fluorocarbon resin is any of those exemplified above.

The side wall 112 only needs to have such a configuration that the plurality of receptacles 113 are provided on the plate-like member 111. For example, the side wall 112 may be a plate-like structure parts of which corresponding to the receptacles 113 are holes.

A height of the side wall 112 measured from the surface of the plate-like member 111 (i.e., a thickness in a vertical direction) only needs to be designed so that one of the beads 121 and 121' once stored in the receptacles 113 would not be again discharged from the receptacles 113 during the step of beads storing. For example, the height of the side wall 112 may be designed so that most part of, preferably the whole part of, one of the beads 121 and 121' stored in one of the receptacles 113 is positioned lower than the upper surface of the side wall 112.

In order to efficiently store the beads 121 and 121' in the receptacles 113, the height of the side wall 112 is preferably equal to or greater than the average particle diameter of the beads 121 and 121'. Further, in order that only one of the beads 121 and 121' is stored in one of the receptacles 113, the height of the side wall 112 is preferably equal to or smaller than 1.5 times the average particle diameter of the beads 121 and 121'.

Each of the plurality of receptacles 113 is a recess capable of storing only one of the beads 121 and 121', and the plurality of receptacles 113 are separated from each other by the side wall 112. Each of the receptacles 113 has a bottom surface which is a part of the surface of the plate-like member 111, and the bottom surface is hydrophilic.

The receptacles 113 can have any shape or size, as long as the shape or size allows each of the receptacles 113 to store only one of the beads 121 and 121' therein. The region surrounded by the bottom surface and the lateral surface of each of the receptacles 113 may be shaped in, e.g., a circular cylindrical or a rectangular column.

A width "w" of each of the receptacles 113 in a horizontal direction (e.g., in a case where a cross section of each receptacle 113 when seen in the horizontal direction is shaped in a circle, the width "w" is a diameter of the circle; in a case where the cross section of each receptacle 113 when seen in the horizontal direction is shaped in a square, the width "w" is a length of one side of the square) only needs to be larger than the average particle diameter of the beads 121 and 121'. Preferably, the width "w" is, for example, 1 to 2 times larger than the average particle diameter of the beads 121 and 121'. In the present embodiment, each of the receptacles 113 has a depth equal to the height of the side wall 112. In order to efficiently store the beads in the receptacles, the depth of each of the receptacles of the present invention is preferably equal to or greater than the average particle diameter of the beads. Further, in order that only one of the beads is stored in one of the receptacles, the depth of each of the receptacles of the present invention is preferably equal to or smaller than 1.5 times the average particle diameter of the beads.

Techniques, such as photolithography, etching, and substrate lamination, for preparing the array 101 are the same as techniques for preparing general-purpose microchips and arrays.

According to the present embodiment, each of the receptacles 113 has a hydrophilic bottom surface, and the side wall 112 has a hydrophobic upper surface. Thus, the first solvent 120 containing the beads 121 and 121' can be efficiently introduced into the receptacles 113 when the hydrophilic first solvent 120 is used in the step of beads introduction. In addition, because the hydrophobic second solvent 130 used in the step of beads storing can be prevented from entering into the receptacles 113, the hydrophilic first solvent 120 in the receptacles 113 can be efficiently hermetically sealed with the hydrophobic second solvent 130 to form droplets (liquid droplets).

The array 101 of the present embodiment may be, for example, an array including one million or more receptacles. Even with the array having such a large area, the use of the method for sealing beads of the present embodiment or the method for detecting a target molecule of the present embodiment makes it possible to efficiently seal the beads into the receptacles so that any one of the beads is stored in each of the receptacles. Thus, according to the present embodiment, it is possible to detect the target molecules with high sensitivity, thereby enabling to provide an array allowing detection of target molecules of such a quite low concentration as approximately 10 aM.

3. Kit

Next, the following describes a configuration of a kit of the present invention.

The kit of the present invention includes at least the array 1 and the beads 41 (refer to the first embodiment) or the array 101 and the beads 121 (refer to the second embodiment). Preferably used as the arrays 1 and 101 are the arrays 1 and 101 having the above-described configuration. Each of the receptacles 13 and 113 in the arrays 1 and 101 is configured to be capable of storing only one of the beads 41 and 121 included in this kit.

Each of the beads 41 and 121 included in this kit may be the one specifically capturing the target molecule. For example, each of the beads 41 included in this kit may be the one having been bound to a molecule for specifically binding to the target molecule. Suitably used as the target molecule and the molecule for specifically binding to the target molecule can be any of those mentioned above.

This kit may further include a substance for specifically detecting the target molecule. Preferably used as the substance for specifically detecting the target molecule may be any of those mentioned above. Furthermore, the kit may further include, e.g., the hydrophilic solvent and the hydrophobic solvent described above, or the first solvent and the second solvent described above, and a surfactant.

4. Target Molecule Detection Device

Figure 3:
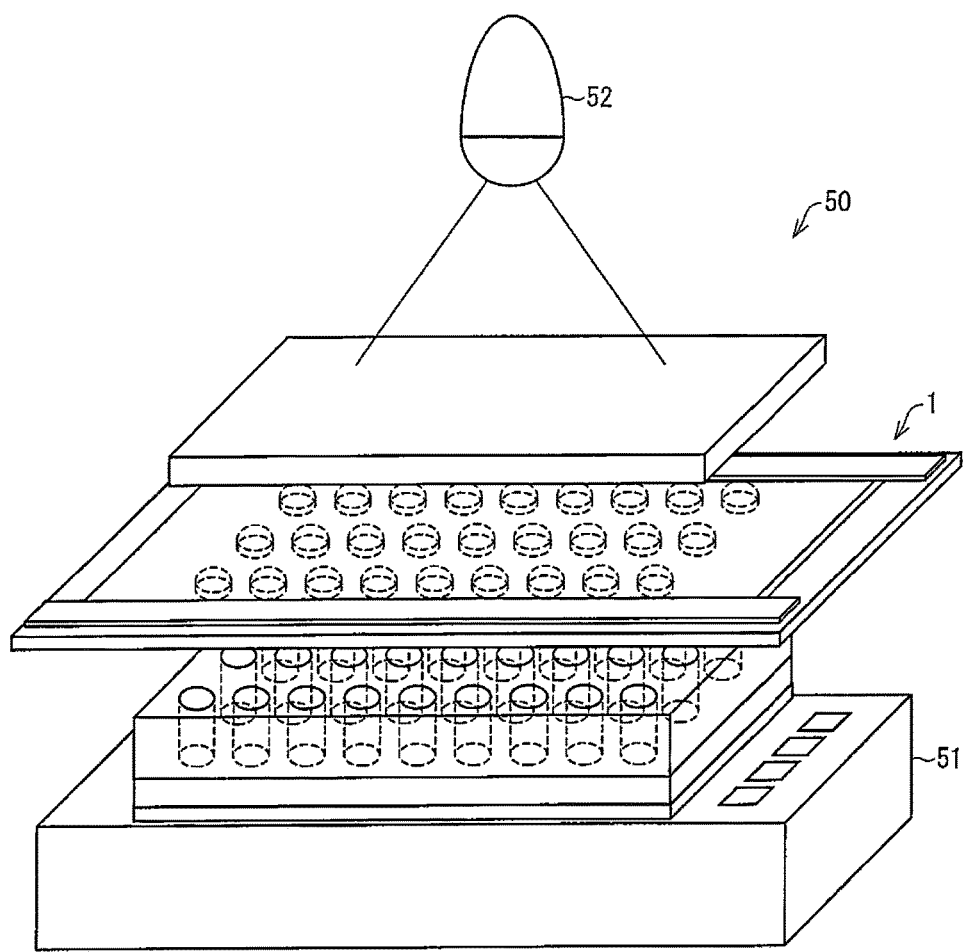
FIG. 3 is a view schematically illustrating one embodiment of a target molecule detection device according to the present invention.

Next, the following describes a target molecule detection device 50 of the present invention with reference to FIG. 3. FIG. 3 is a view schematically illustrating one embodiment of a target molecule detection device according to the present invention.

The target molecule detection device 50 of the present invention includes the array 1 or the array 101 (hereinafter collectively referred to simply as the "array 1"), an image sensor 51, and a light source 52. Preferably used as the array 1 may be the one having the above-described configuration, and therefore explanations of the array 1 are omitted here.

The image sensor 51 is a sensor for detecting light emitted by each of the receptacles 13 or the receptacles 113 (hereinafter collectively referred to simply as the "receptacles 13") when the beads having captured the target molecules are stored in the receptacles 13. For example, the image sensor 51 may be a sensor for detecting fluorescence emitted by a fluorescent substrate when decomposed by a certain enzyme bound to (i) the target molecule or (ii) a molecule specifically bound to the target molecule. Suitably used as the image sensor 51 can be, for example, a CMOS image sensor.

The light source 52 is a light source for emitting light to the array 1. In FIG. 3, the light source 52 is provided above the array 1. However, the present invention is not particularly limited to this. Alternatively, the light source 52 may be the one emitting light to a lateral side of the array 1, for example.

Between the array 1 and the image sensor 51, an interference filter and/or a light guide array may be provided, for example. Further, between the light source 52 and the array 1, an excitation filter may be provided, for example.

According to the present embodiment, the array 1 and the image sensor 51 are directly connected with each other. This makes it possible to easily determine, without use of other device such as a microscope, whether or not any one of the beads having captured the target molecules is stored in each of the receptacles 13. This enables to carry out easy and high-speed detection of whether or not any one of the beads captured the target molecules is stored in each of the receptacles 13, and to provide the target molecule detection device at an affordable price.

5. Application Example of Method for Sealing Substance According to Present Invention In the method for sealing a substance according to the present invention, the substance sealed in the receptacles provided on the substrate may be beads, nucleic acid, protein, virus, cells, lipid membrane complex, or the like. In the above embodiment, the method has been described using beads as an example.

According to the present invention, the nucleic acid includes DNA and RNA. The protein and the virus include polymers (oligomers) thereof and complexes thereof with other substances. The cells include, particularly, bacterial cells, and the lipid membrane complex includes, particularly, liposome and exosome, and further cell organelle, such as mitochondria.

When the subject of sealing is nucleic acid, protein, virus, cells, lipid membrane complex, or the like, the method for sealing a substance according to the present invention can be used in applications, such as ELISA-PCR.

The present invention is not limited to the description of the embodiments above, but may be altered by a skilled person within the scope of the claims. The embodiments of the present invention are described in further detail via the following Examples. Needless to say, the present invention is not limited to these Examples. The invention being thus described, it will be clear that the same may be varied in many ways.

EXAMPLES

The following will describe materials and methods that were used in Examples.
(Materials)
In the Examples, used as the target molecule was streptavidin (purchased from SIGMA) labeled with (3-galactosidase (hereinafter, also simply referred to as "streptavidin"). Further, used as the beads were biotinylated beads prepared by biotinylating amino beads having an average particle diameter of 3 μm (material: polystyrene; micromer-$NH_2$-3 μm; purchased from Micromod).
Preparation of Biotinylated Beads
By the following method, amino groups of amino beads were reacted with NHS-PEO4-Biotin, so that the amino beads were biotinylated.

First, 750 μL of buffer A (100 mM phosphoric acid buffer, pH 8.0) was added to 250 μL of amino beads dispersion (50 mg/ml, approximately $3.4*10^9$ beads/mL).

Next, the resultant was subjected to centrifugation at 10000 rpm at 4° C. for 10 minutes, so that the amino beads were gathered up and collected. Then, the amino beads were suspended in 500 μL of buffer A (suspension A). Thereafter, 50 μL of NHS-PEO4-Biotin (2 μg/50 μL DMSO) was added to the suspension A, and then the amino beads and NHS-PEO4-Biotin were reacted under gentle stirring at 25° C. for at least 3 hours (the tube was rotated end-over-end for mixing).

Next, biotinylated beads thus obtained were washed. The mixture was subjected to centrifugation at 10000 rpm at 4° C. for 10 minutes, so that the biotinylated beads were gathered up and collected. Then, an aqueous phase therein was removed by a Pipetman pipette. To the resulting precipitate of the biotinylated beads, 1 mL of buffer A was added so that the precipitate of the biotinylated beads was suspended. This process was repeated six times, so that unreacted NHS-PEO4-Biotin was removed. Then, the resultant was suspended in 500 μL of buffer A (suspension B). The suspension B was preserved at 4° C.

Next, a concentration of the biotinylated beads in the suspension B was measured. The number of biotinylated beads in a certain volume was counted by use of a hemacytometer, so that the concentration of the biotinylated beads was found (approximately $3.0*10^8$ beads/mL). In order that the number of biotinylated beads was easily counted, the counting was carried out after the suspension B was diluted by the buffer A by approximately 5-fold, for example.

By the above-mentioned method, the biotinylated beads were obtained.

(Capturing of Streptavidin)

Next, by the following method, streptavidin was captured by use of the biotinylated beads.

First, the biotinylated beads were diluted ($8*10^6$ beads/500 µL). Further, streptavidin labeled with β-galactosidase was diluted by the buffer B (100 mM phosphoric acid buffer, pH 8.0, containing 0.1% TWEEN20 (detergent)) so that a concentration of streptavidin became two times higher than a target concentration (total amount: 500 µL).

Then, 500 µL of the biotinylated beads and 500 µL of streptavidin thus diluted were mixed together in a tube (total amount: 1 mL). The tube was shaken vertically in a gentle manner, so that reaction between the biotinylated beads and streptavidin was carried out at 25° C. for 30 minutes.

Next, the resultant was subjected to centrifugation at 10000 rpm at 4° C. for 10 minutes, so that the beads after the reaction (a mixture of (i) complexes of streptavidin and the biotinylated beads and (ii) unreacted biotinylated beads) were gathered up and collected. Then, an aqueous phase therein was removed by a Pipetman pipette. To the resulting precipitate of beads, 1 mL of buffer A was added and suspended. This process was repeated four times for washing, so that unreacted target molecules were removed.

Next, to the precipitate of the beads after the washing, 15 µL of buffer C (100 mM phosphoric acid buffer, pH 7.5, 1 mM $MgCl_2$) was added for suspension. An ultimate concentration of the beads was approximately $6.5*10^6$ beads/15-µL buffer C.

(Production of Array)

Next, by the following method, an array having the same flow cell structure as that of the array 1 shown in (a) through (e) of FIG. 1 was produced. In the following descriptions, members having the same functions as those in the array 1 are given the same reference signs.

First, a hydrophilic-hydrophobic patterned glass (lower layer section 10) and an upper side glass (upper layer section 20) (height: 24 mm*width: 26 mm*depth: 5 mm, $SiO_2$, with a through-hole having a diameter of 1 mm) were prepared.

(Preparation of Hydrophilic-Hydrophobic Patterned Glass)

With reference to FIG. 8, the following describes a specific method for preparing the hydrophilic-hydrophobic patterned glass. FIG. 8 is a view for explaining a method for preparing a hydrophilic-hydrophobic patterned glass according to an example of the present invention.

According to the present embodiment, photolithography and dry etching were carried out so that a hydrophilic-hydrophobic pattern was formed on glass. In order to form the hydrophilic-hydrophobic pattern, three steps including a step of CYTOP (Registered Trademark) application, a step of photolithography, and a step of etching and resist removal were carried out.

In the step of CYTOP (Registered Trademark) application, CYTOP (Registered Trademark) CTL-809 (product name; available from ASAHI GLASS) was first applied onto glass of 24 mm (height)*32 mm (width) (product name: NEO MICRO COVER GLASS Thickness No. 1; available from MATSUNAMI) (plate-like member 11), so that a hydrophobic resin layer 61 was formed.

Next, in the step of photolithography, a positive photoresist 62 (product name: AZ-4903; available from AZ Electronic Materials USA) was applied onto the hydrophobic resin layer 61. Next, via a photomask 63 having a desired pattern, the resultant was exposed to UV emitted from above, so that an alkaline development process was carried out. As a result of the development process, the photoresist 62 was dissolved only in parts irradiated with UV, so that parts of the hydrophobic resin layer 61 which parts faced the parts of the photoresist 62 irradiated with UV were exposed.

After that, in the step of etching and resist removal, the glass was etched by $O_2$ plasma via a partially dissolved photoresist 62', so that the parts of the resin layer 61 were removed. As a result, a hydrophobic side wall 12 was obtained. Finally, the photoresist 62' was dissolved by an organic solvent. Thus, the hydrophilic-hydrophobic pattern was obtained.

Further detailed procedures for the above process are described below. The reference numerals (1) through (23) in FIG. 8 correspond to (1) through (23) below, respectively.

<Step of CYTOP (Registered Trademark) Application (i.e., Preparation of CYTOP (Registered Trademark) Layer Having Film Thickness of Approximately 3.3 µm to 3.5 µm by the Following Procedures)>

(1) First, glass (plate-like member 11) was washed and CYTOP (Registered Trademark) CTL-809 was applied onto the glass.

(2) Next, the glass was immersed in 10N KOH overnight.

(3) The cover glass having been immersed in KOH was washed with deionized water ten or more times.

(4) The glass was dried with a hot plate at 180° C.

(5) The glass thus dried was cooled to room temperature.

(6) Approximately 70 µL of CYTOP (Registered Trademark) CTL-809 was poured onto the glass.

(7) Spin-coating was carried out according to the following program A:

[Program A]
Slope: 5 seconds
500 rpm: 10 seconds
Slope: 5 seconds
2000 rpm: 30 seconds
Slope: 5 seconds
End (8) The glass was baked on the hot plate at 180° C. for an hour.

By repeating the above procedures (6) through (8) four times, a hydrophobic resin layer 61 having a thickness of 3.3 µm to 3.5 µm was obtained.

<Step of Photolithography>

Next, photolithography was carried out.

(9) Onto the resin layer 61 prepared by the step of CYTOP (Registered Trademark) application, a positive photoresist 62 (AZ-4903) was poured in such an amount that the poured positive photoresist 62 spread on the glass so as to be in a diameter of approximately 8 mm.

(10) Spin-coating was carried out according to the following program B:

[Program B]
Slope: 5 seconds
500 rpm: 10 seconds
Slope: 5 seconds
4000 rpm: 60 seconds
Slope: 5 seconds
End

(11) The photoresist remaining on an edge of the glass was wiped out with a piece of gauze dampened with 100% EtOH.

(12) The glass was baked at 55° C. for 3 minutes.

(13) The glass was baked at 110° C. for 5 minutes.

(14) A photomask 63 was washed with acetone, and then the photomask 63 was set in a mask aligner (available from SAN-EI ELECTORIC).

(15) The glass to which the photoresist 62 was applied was set on a sample table of the mask aligner, and the sample table was lifted up, so that the glass and the photomask 63 were brought into contact with each other.

(16) The glass thus brought into contact with the photomask 63 was irradiated with UV for 35 seconds (power: 256 W/cm$^2$).

(17) The glass was immersed in AZ Developer (available from AZ Electronic Materials USA) for 5 minutes or more for development.

(18) The glass was rinsed with MilliQ (distilled water) for approximately 10 minutes.

<Step of Etching and Resist Removal>

Subsequently, etching and removal of the resist were carried out.

(19) The glass was subjected to O$_2$ plasma etching by use of RIE-10NR (available from Samco) under certain process conditions (O$_2$: 50 sccm, pressure: 10 Pa, power: 50 W, time: 30 min.).

(20) The glass having been subjected to the etching was immersed in acetone, and then the glass was sonicated for 15 minutes.

(21) Acetone was exchanged for new one, and then the glass was sonicated again for 15 minutes.

(22) The glass was sonicated in EtOH for 15 minutes.

(23) The glass was washed with MilliQ (distilled water).

In the above-described method, a plurality of wells (receptacles 13) were formed on the glass. A region surrounded by the bottom surface and the lateral surface of each of the wells was shaped in a circular cylinder. A cross section of each well in the horizontal direction was shaped in a circle having a diameter of 5 μm. A height of the side wall, by which the wells were partitioned, was approximately 3.3 μm to 3.5 μm. Further, a distance (refer to the reference sign "B" in FIG. 1), by which two adjacent wells were separated from each other, was 5 μm.

(Preparation of Upper Side Glass)

In the following method, an upper side glass was prepared. In order to prepare the upper side glass, such glass was used that has a thickness of 5 mm and a through-hole having a diameter of 1 mm. One side of this glass was covered with approximately 70 μL of CYTOP (Registered Trademark) CTL-809 (product name; available from ASAHI GLASS). Then, spin-coating was carried out according to the following program C:

[Program C]
Slope: 5 seconds
500 rpm: 10 seconds
Slope: 5 seconds
2000 rpm: 30 seconds
Slope: 5 seconds
End Thereafter, the glass was baked on a hot plate at 180° C. for an hour.

In the above-described method, an upper side glass having one side provided with a hydrophobic layer of a thickness of 1 μm was prepared.

(Bonding of Hydrophilic-Hydrophobic Patterned Glass and Upper Side Glass)

Next, high vacuum grease (available from DOW CORNING TORAY) was applied to a piece of backing paper of Parafilm (available from Peckiney Plastic Packaging), and then the piece of backing paper of Parafilm was attached onto a part of the hydrophilic-hydrophobic patterned glass, the part being on a side on which the hydrophilic-hydrophobic pattern was formed, and the part not having the hydrophilic-hydrophobic pattern. The upper side glass was bonded to the side of the hydrophilic-hydrophobic patterned glass on which side the hydrophilic-hydrophobic pattern was formed, in such a manner that the coating agent-coated side of the upper side glass faced the hydrophilic-hydrophobic patterned glass.

Consequently, a space was made between the hydrophilic-hydrophobic patterned glass and the upper side glass. A width of this space in the vertical direction, i.e., a distance between (i) the upper surface of the side wall of the hydrophilic-hydrophobic patterned glass and (ii) the upper side glass was approximately 150 μm.

(Sealing of Beads into Droplets)

Next, in the following method, the beads having been reacted with streptavidin were sealed into droplets.

First, 50 mM fluorescein-di-β-galactopyranoside (FDG) (available from Marker Gene Technology)/DMSO was diluted with FDG buffer (100 mM KPi buffer (PH=7.5), 1 mM MgCl$_2$, 4 μL/mL 2-mercaptethanol), so that 4 mM FDG solution was prepared. Then, 15 μL of the beads (6.5*10$^6$ beads/15-μL buffer C) and 15 μL of 4 mM FDG solution were mixed together, so that a beads solution was prepared.

Next, 30 μL of the beads solution was loaded into the flow path by a yellow tip via the through-hole of the upper side glass (see (a) and (b) of FIG. 1).

Next, in order to remove the air in the wells, deaeration was carried out for one minute (see (c) of FIG. 1). The deaeration was carried out in such a manner that the array was allowed to stand still in a vacuum desiccator of approximately 0.1 atm for approximately 30 seconds. After that, the array was left at rest for approximately 5 minutes, so that the beads were precipitated into the bottoms of the wells.

Thereafter, 200 μL to 1000 μL of Fluorinert (Registered Trademark) FC40 (available from SIGMA) was loaded into the flow path via the through-hole of the upper side glass (see (d) and (e) of FIG. 1).

As a result, an aqueous phase was trapped only in the wells, so that droplets were formed. Thus, the beads were sealed into the droplets.

Example 1

By the above-described method, biotinylated beads and 1 fM streptavidin were reacted with each other, and then the resultant was introduced into an array together with FDG, so that the beads were sealed into droplets, respectively. The array used in Example 1 was a 1.0 cm*1.0 cm array including a total of 1097600 receptacles, specifically, including a 20*20 (horizontally and vertically) matrix of subarrays each (i) having a size of 512 μm*512 μm and (ii) including 2744 receptacles. This array was observed with a fluorescence microscope (IX71 (available from OLYMPUS)).

Figure 4:
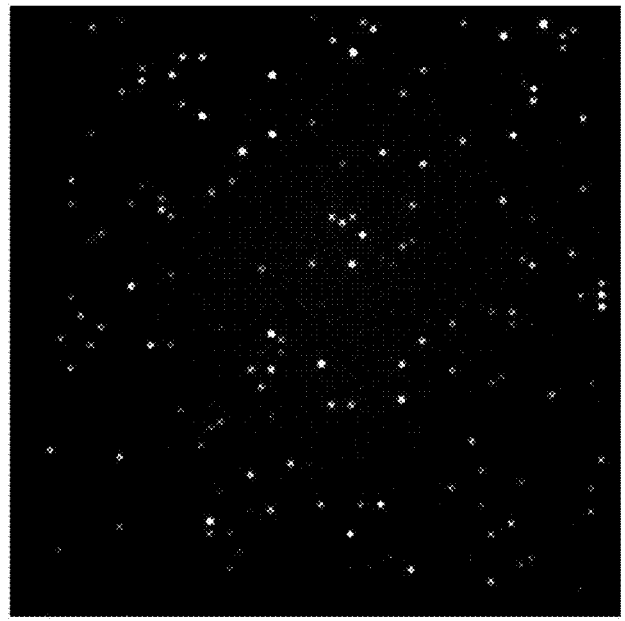
FIG. 4 shows a fluorescence image of an array into which beads were sealed in Example 1.

FIG. 4 shows a fluorescence image of the array into which the beads were sealed in one example of the present invention. What is shown in FIG. 4 is one subarray. As shown in FIG. 4, some bright points were observed in the fluorescence image (138 bright points in one field). These bright points indicate positions of receptacles into which biotinylated beads having captured streptavidin were sealed. This shows that the use of the method of the present invention makes it possible to adequately detect 1 fM streptavidin.

Comparative Example 1

In a comparative example of the present invention, target molecules were detected by a conventional bulk measurement method.

12.5 fM streptavidin, which is 12.5 times higher concentration than that (1 fM) in Example 1, was mixed with FDG, and the resultant was measured for fluorescence by a fluorescence spectrophotometer. Further, a control experiment was carried out in the same manner by use of 6.3 pM streptavidin, which is 500 times higher concentration than that of this comparative example.

Figure 5:
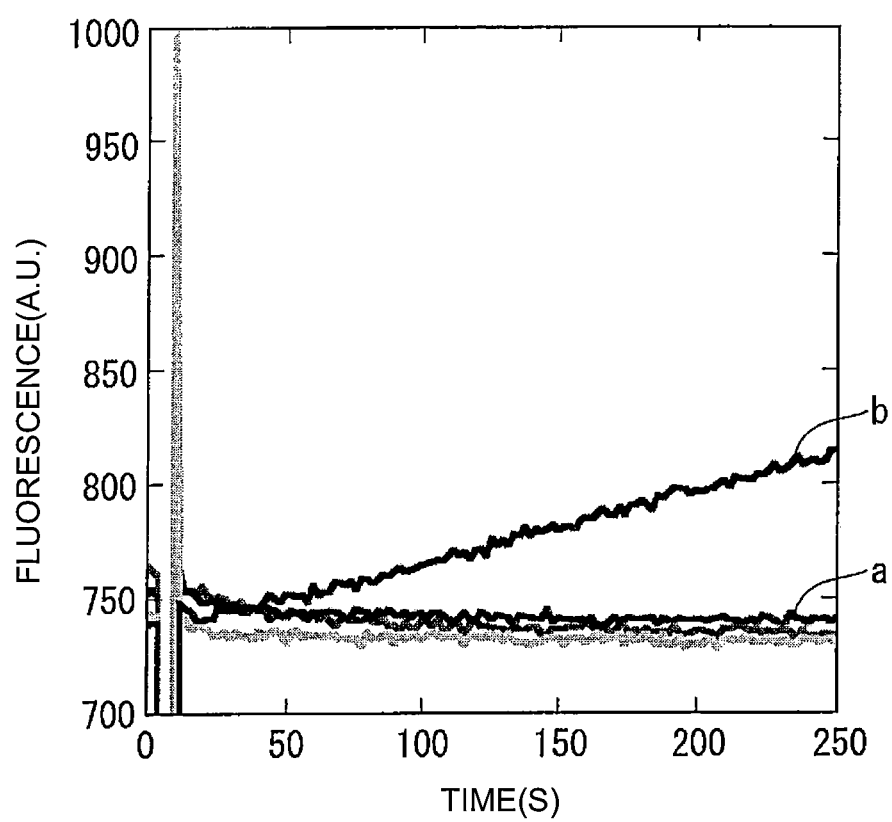
FIG. 5 is a graph showing fluorescence intensities observed when target molecules were detected by a conventional method.

FIG. 5 shows results of the comparative example and the control experiment. FIG. 5 is a graph showing fluorescence intensities observed when the target molecules were detected by the conventional method. In FIG. 5, a graph line "a" shows a result of the case involving use of 12.5 fM streptavidin (number of test groups: 3), whereas a graph line "b" shows a result of the case involving use of 6.3 pM streptavidin.

As shown in FIG. 5, in the case where the conventional method was used, it was impossible to detect 12.5 fM streptavidin. This shows that 12.5 fM is lower than a detection limit of the conventional method.

Example 2

Next, biotinylated beads were reacted with streptavidin of five different concentrations (1 fM, 100 aM, 10 aM, 1 aM, and 0.1 aM), and then were introduced into arrays together with FDG, so that the beads were sealed into droplets, respectively. Each of the arrays used in Example 2 had the same configuration as that used in Example 1. Each of these arrays was observed in a bright field image and in a fluorescence image by a microscope.
(Detection Results)

(a) through (f) of FIG. 6 show microscopic images of the arrays into which the beads were sealed. Note that each of (a), (c), and (e) of FIG. 6 shows a bright field image of a respective one of subarrays, whereas each of (b), (d), and (f) of FIG. 6 shows a fluorescence image of a respective one of the subarrays shown in (a), (c), and (e) of FIG. 6. Further, (a) and (b) of FIG. 6 show the results obtained in the case involving the use of 1 fM streptavidin; (c) and (d) of FIG. 6 show the results obtained in the case involving the use of 100 aM streptavidin; and (e) and (f) of FIG. 6 show the results obtained in the case involving the use of 10 aM streptavidin.

In the case involving the use of 1 fM streptavidin, a total number of beads sealed into one subarray was 1735; among those beads, the number of beads having captured streptavidin was 138. In the case involving the use of 100 aM streptavidin, a total number of beads sealed into one subarray was 2008; among those beads, the number of beads having captured streptavidin was 6. In the case involving the use of 10 aM streptavidin, a total number of beads sealed into one subarray was 1360; among those beads, the number of beads having captured streptavidin was 1.
(Comparison Between Theoretical Value and Experimental Value)

Further, a theoretical value and an experimental value of a ratio (%) of the number of beads (active beads) having captured streptavidin with respect to the total number of beads were calculated for each of the streptavidin concentrations.

Calculated as the theoretical value was a ratio (%) of the number of streptavidin molecules with respect to the total number of beads used in the reaction with streptavidin. Whereas, calculated as the experimental value was a ratio (%) of the number of beads having captured streptavidin with respect to the number of beads stored in the array.

FIG. 7 shows a graph illustrating a relationship between (i) a concentration of streptavidin and (ii) a ratio of the number of beads having captured streptavidin with respect to the number of beads stored in the array. In FIG. 7, a graph line "a" shows the theoretical values, a circular dot shows the experimental value, and a circle drawn with a dotted line shows averages of the experimental values (N=2 to 3). Further, a graph line "b" is a line by which averages of the experimental values were approximated.

As shown in FIG. 7, the theoretical values and the experimental values are almost the same as each other. This shows that the method of the present example has a high quantitative accuracy, and is capable of accurately measuring a concentration of target molecules. These results show that the method of the present example makes it possible to adequately detect even target molecules of 0.1 aM or so.

Example 3

By the above-described method, a beads solution (6.5*10$^6$ beads/30 μL) was introduced (loaded) into the array having the flow cell structure prepared in Example 1, so that the beads were sealed (trapped) into droplets. Then, a trapping efficiency (i.e., a ratio (%) of the number of trapped beads with respect to the number of loaded beads) during this process was calculated.

A result of the calculation is shown in FIG. 9. FIG. 9 is a view illustrating (i) a bead trapping efficiency found in a case involving the use of the array having the flow cell structure (Example 3) and (ii) a bead trapping efficiency found in a case involving the use of an array not having the flow cell structure (Example 4).

Example 4

In this comparative example, the array not having the flow cell structure (i.e., the array made of the above-described hydrophilic-hydrophobic patterned glass only; see FIG. 2) was used for beads sealing (amino beads of Φ=3 μm; micromer-NH$_2$-3 μm; available from micromod).

By the below-described method, beads were sealed into the hydrophilic-hydrophobic patterned glass by use of a beads solution which was diluted at the same concentration (2.2*10$^8$ beads/mL=6.5*10$^6$ beads/30 μL) as that used in the case involving the use of the array having the flow cell structure (Example 3).

(1) The beads were diluted at a concentration of 2.2*10$^8$ beads/mL with a buffer (100 mM KPi buffer (PH=7.5), 1 mM MgCl$_2$, 2 μL/mL 2-mercaptethanol).

(2) The hydrophilic-hydrophobic patterned glass (prepared by the above-mentioned method) was bonded to a bottom of a petri dish (35-mm petri dish, available from Becton Dickinson). An adhesive used therefor was Araldite AR-R30 (available from NICHIBAN).

(3) An upper surface of the hydrophilic-hydrophobic patterned glass was covered with 500 μL of the beads solution.

(4) The resultant was subjected to deaeration, and then was incubated for 5 minutes.

(5) 2 mL of FC40 (Fluorinert (Registered Trademark) FC40, available from SIGMA) was loaded onto the hydrophilic-hydrophobic patterned glass, so that the beads were sealed thereinto.

After that, the number of beads confined in the droplets was counted, and then a trapping efficiency (a ratio (%) of the number of trapped beads with respect to the number of loaded beads) was calculated.

Results of the calculations are shown in FIG. 9. As shown in FIG. 9, in the case involving the use of the array having the flow cell structure, 8.4% of the beads could be trapped. Further, in the case involving the use of the array not having the flow cell structure, 0.33% of the beads could be trapped. For reference, the appearance of layer substitution in laminating FC40 (colorless) on the layer of a beads solution (colored in red) introduced by the procedure of (3) above is shown in FIG. 10. FIG. 10A visualizes the lamination of the FC40 layer on the beads solution layer; FIG. 10B, the precipitation of FC40 after lamination; and 10C and 10D, the layer substitution between the beads solution layer and the FC40 layer. For reference, FIG. 11 shows a microscopic image of an array in which beads are sealed by the procedure of (5) above, and its magnified image.

INDUSTRIAL APPLICABILITY

The present invention is suitably applicable to a method for detecting target molecules of low concentration, an array therefor, a device therefor, and the like.

REFERENCE SIGNS LIST

1: Array
10: Lower layer section
20: Upper layer section
12: Side wall
13: Receptacle
30: Space
41, 41': Beads
42: Hydrophilic solvent
43: Hydrophobic solvent
101: Array
110: Substrate
111: Plate-like Member
112: Side Wall
113: Receptacle
114: Region
120: First Solvent
121, 121': Beads
130: Second Solvent

The invention claimed is:
1. A method for sealing a bead in a receptacle, the method comprising:
(i) a step of introducing a first solvent containing beads and a surfactant on a substrate,
wherein
the substrate has a hydrophilic surface,
a plurality of receptacles capable of storing the beads are formed, separated from each other by a side wall having a height, on the hydrophilic surface of the substrate,
the side wall is made of a hydrophilic structure,
a hydrophobic layer is formed on an upper surface of the side wall,
the height of the side wall is equal to or greater than an average particle diameter of the beads, and equal to or smaller than 1.5 times the average particle diameter of the beads, and
the plurality of receptacles each have a width that is 1 to 2 times larger than the average particle diameter of the beads; and
(ii) a step of introducing a second solvent having a greater specific gravity than that of the first solvent onto the first solvent so that the second solvent laminated onto the first solvent moves down below the first solvent due to its greater specific gravity than that of the first solvent and thereby the first solvent is substituted by the second solvent, thereby to form droplets of the first solvent within the plurality of receptacles covered with the second solvent, the step (ii) being carried out after the step (i);
wherein
at least one of the droplets of the first solvent formed within the plurality of receptacles covered with the second solvent contains one of the beads.

2. The method as set forth in claim 1, wherein the surfactant is polyoxyethylene sorbitan monolaurate or polyethylene glycol mono-4-octylphenyl ether.

3. The method as set forth in claim 1, wherein the surfactant has a concentration of 0.001% by weight to 1% by weight.

4. The method as set forth in claim 1, wherein the surfactant has a concentration of 0.01% by weight to 0.1% by weight.

5. The method as set forth in claim 1, wherein the surfactant has a concentration of 0.01% by weight to 0.05% by weight.

6. The method as set forth in claim 1, wherein the second solvent is at least one selected from the group consisting of saturated hydrocarbon, unsaturated hydrocarbon, aromatic hydrocarbon, silicone oil, hexafluoropropylene epoxide polymer, a polymer having a hydrofluoroether structure, perfluoropolyether, chlorotrifluoroethylene polymer, and a polymer having a perfluorocarbon structure, or is a mixed solvent that includes at least one of these solvents.

7. The method as set forth in claim 1, wherein the first solvent is at least one selected from the group consisting of water, hydrophilic alcohol, hydrophilic ether, ketone, nitrile solvents, dimethyl sulfoxide, and N,N-dimethylformamide, or is a mixed solvent that includes at least one of these solvents.

8. A method for detecting a target molecule selected from the group consisting of a protein, a nucleic acid, a sugar, and a virus particle, the method comprising:
(i) a step of reacting with target molecules, beads specifically capturing the target molecules by target-capturing molecules bound to the beads, the target-capturing molecule selected from the group consisting of a protein, an antibody, and a nucleic acid;
(ii) a step of introducing a first solvent containing the beads of the step (i) and a surfactant on a substrate,
wherein
the substrate has a hydrophilic surface,
a plurality of receptacles capable of storing the beads are formed, separated from each other by a side wall having a height, on the hydrophilic surface of the substrate,
the side wall is made of a hydrophilic structure,
a hydrophobic layer is formed on an upper surface of the side wall,
the height of the side wall is equal to or greater than an average particle diameter of the beads, and equal to or smaller than 1.5 times the average particle diameter of the beads, and
the plurality of receptacles each have a width that is 1 to 2 times larger than the average particle diameter of the beads,
the step (ii) being carried out after the step (i);
(iii) a step of introducing a second solvent having a greater specific gravity than that of the first solvent onto the first solvent so that the second solvent laminated onto the first solvent moves down below the first solvent due to its greater specific gravity than that of the first solvent and thereby the first solvent is substituted by the second solvent, thereby to form droplets of the first solvent within the plurality of receptacles covered with the second solvent, the step (iii) being carried out after the step (ii); and (iv) a step of detecting the target molecule to determine whether or not any one of beads having captured the target molecule is stored in each of the plurality of the receptacles by use of a fluorescence microscope or an image sensor, the step (iv) being carried out after the step (iii).

9. The method as set forth in claim 8, wherein the step (i) is preceded by a step of binding to the beads, the target-capturing molecules.

10. The method as set forth in claim 8, wherein the second solvent is at least one selected from the group consisting of saturated hydrocarbon, unsaturated hydrocarbon, aromatic hydrocarbon, silicone oil, hexafluoropropylene epoxide polymer, a polymer having a hydrofluoroether structure, perfluoropolyether, chlorotrifluoroethylene polymer, and a polymer having a perfluorocarbon structure, or is a mixed solvent that includes at least one of these solvents.

11. The method as set forth in claim 8, wherein the first solvent is at least one selected from the group consisting of water, hydrophilic alcohol, hydrophilic ether, ketone, nitrile solvents, dimethyl sulfoxide, and N,N-dimethylformamide, or is a mixed solvent that includes at least one of these solvents.

* * * * *